US011302005B2

(12) United States Patent
Tanji

(10) Patent No.: US 11,302,005 B2
(45) Date of Patent: Apr. 12, 2022

(54) BONE CUTTING SUPPORT SYSTEM, INFORMATION PROCESSING APPARATUS, IMAGE PROCESSING METHOD, AND IMAGE PROCESSING PROGRAM

(71) Applicant: Atsushi Tanji, Tokyo (JP)

(72) Inventor: Atsushi Tanji, Tokyo (JP)

(*) Notice: Subject to any disclaimer, the term of this patent is extended or adjusted under 35 U.S.C. 154(b) by 0 days.

(21) Appl. No.: 16/596,223

(22) Filed: Oct. 8, 2019

(65) Prior Publication Data

US 2020/0043168 A1 Feb. 6, 2020

Related U.S. Application Data

(63) Continuation of application No. 14/898,021, filed as application No. PCT/JP2014/065448 on Jun. 11, 2014, now Pat. No. 10,467,752.

(30) Foreign Application Priority Data

Jun. 11, 2013 (JP) .................................. 2013-123210

(51) Int. Cl.
*G06K 9/00* (2006.01)
*G06T 7/00* (2017.01)
(Continued)

(52) U.S. Cl.
CPC .......... *G06T 7/0014* (2013.01); *A61B 17/152* (2013.01); *A61B 34/10* (2016.02);
(Continued)

(58) Field of Classification Search
CPC ............ A61B 17/152; A61B 2034/105; A61B 2034/107; A61B 34/10; G06T 17/00;
(Continued)

(56) References Cited

U.S. PATENT DOCUMENTS 4,841,975 A * 6/1989 Woolson ............... A61B 17/154
378/205
6,241,735 B1 * 6/2001 Marmulla ............... A61B 34/70
606/102
(Continued)

FOREIGN PATENT DOCUMENTS

JP 2001-507614 A 6/2001
JP 2005-525868 A 9/2005
(Continued)

OTHER PUBLICATIONS

Cartiaux, Olivier, et al. "Computer-assisted planning and navigation improves cutting accuracy during simulated bone tumor surgery of the pelvis." Computer Aided Surgery 18.1-2 (2013): 19-26. (Year: 2013).*

(Continued)

*Primary Examiner* — Stephen P Coleman
(74) *Attorney, Agent, or Firm* — Ladas & Parry LLP

(57) ABSTRACT

A system of this invention is directed to a bone cutting support system that properly indicates a bone cutting plane determined in advance to a doctor during surgery. The bone cutting support system includes a storage that stores 3D shape data of a surgery target bone in association with position data of a marker fixed to the surgery target bone, a bone cutting plane determiner that determines, based on the 3D shape data of the surgery target bone, a position and direction of a bone cutting plane or a bone cutting guide plane representing a plane to guide for cutting the surgery target bone, and a bone cutting plane display that displays the determined bone cutting plane based on an image obtained by capturing the marker fixed to the surgery target bone.

11 Claims, 31 Drawing Sheets

(51) Int. Cl.
  *G06T 19/00* (2011.01)
  *A61B 17/15* (2006.01)
  *A61B 34/10* (2016.01)
  *G06T 17/00* (2006.01)

(52) U.S. Cl.
  CPC .............. *G06T 17/00* (2013.01); *G06T 19/00* (2013.01); *A61B 2034/105* (2016.02); *A61B 2034/107* (2016.02); *G06T 2200/04* (2013.01); *G06T 2207/10081* (2013.01); *G06T 2207/30008* (2013.01); *G06T 2207/30204* (2013.01); *G06T 2210/41* (2013.01); *G06T 2219/008* (2013.01)

(58) Field of Classification Search
  CPC ................. G06T 19/00; G06T 2200/04; G06T 2207/10081; G06T 2207/30008; G06T 2207/30204; G06T 2210/41; G06T 2219/008; G06T 7/0014
  USPC ......................................................... 382/131
  See application file for complete search history.

(56) References Cited

U.S. PATENT DOCUMENTS

| | | | | |
|---|---|---|---|---|
| 6,430,434 | B1* | 8/2002 | Mittelstadt | A61B 17/175 600/426 |
| 6,701,174 | B1 | 3/2004 | Krause | |
| 6,711,432 | B1* | 3/2004 | Krause | A61B 17/15 128/922 |
| 7,001,346 | B2* | 2/2006 | White | A61B 90/06 600/587 |
| 7,104,997 | B2* | 9/2006 | Lionberger | A61B 17/155 606/88 |
| 7,217,276 | B2* | 5/2007 | Henderson | A61B 90/36 606/130 |
| 7,388,972 | B2* | 6/2008 | Kitson | G16H 30/40 382/128 |
| 7,392,076 | B2* | 6/2008 | Moctezuma de La Barrera | A61B 17/155 600/407 |
| 2003/0114752 | A1* | 6/2003 | Henderson | A61B 90/36 600/433 |
| 2004/0039259 | A1* | 2/2004 | Krause | G06T 15/20 600/300 |
| 2004/0068187 | A1* | 4/2004 | Krause | A61B 17/15 600/443 |
| 2005/0096535 | A1* | 5/2005 | de la Barrera | A61B 90/36 600/424 |
| 2005/0113846 | A1* | 5/2005 | Carson | A61B 90/36 606/130 |
| 2005/0182320 | A1 | 8/2005 | Stiffer et al. | |
| 2005/0234332 | A1* | 10/2005 | Murphy | A61B 34/20 600/426 |
| 2005/0234465 | A1* | 10/2005 | McCombs | A61B 17/155 606/88 |
| 2006/0015120 | A1* | 1/2006 | Richard | A61B 90/06 606/102 |
| 2007/0073136 | A1* | 3/2007 | Metzger | A61B 17/1675 600/407 |
| 2007/0255288 | A1 | 11/2007 | Mahfouz | |
| 2007/0279435 | A1* | 12/2007 | Ng | G06F 3/011 345/624 |
| 2007/0293755 | A1 | 12/2007 | Shirahata | |
| 2008/0269596 | A1* | 10/2008 | Revie | A61F 2/4603 600/424 |
| 2008/0306490 | A1* | 12/2008 | Lakin | A61B 5/064 606/130 |
| 2008/0319491 | A1* | 12/2008 | Schoenefeld | A61B 90/37 606/86 R |
| 2009/0163923 | A1* | 6/2009 | Flett | A61B 17/17 606/89 |
| 2010/0076563 | A1* | 3/2010 | Otto | A61B 5/4528 623/20.14 |
| 2010/0316268 | A1 | 12/2010 | Liang | |
| 2011/0087465 | A1 | 4/2011 | Mahfouz | |
| 2011/0214279 | A1 | 9/2011 | Park | |
| 2011/0257653 | A1* | 10/2011 | Hughes | A61B 34/10 606/79 |
| 2011/0275957 | A1* | 11/2011 | Bhandari | A61B 34/20 600/595 |
| 2012/0010710 | A1* | 1/2012 | Frigg | A61B 34/20 623/16.11 |
| 2013/0060146 | A1* | 3/2013 | Yang | A61B 6/032 600/476 |
| 2013/0060278 | A1* | 3/2013 | Bozung | A61B 17/00234 606/205 |
| 2013/0061046 | A1 | 3/2013 | Yang | |
| 2013/0293578 | A1* | 11/2013 | Leung | A61B 34/20 345/633 |
| 2013/0322727 | A1 | 12/2013 | Goto | |
| 2014/0193789 | A1 | 7/2014 | Imanaka | |
| 2015/0133764 | A1 | 5/2015 | Sakuragi | |
| 2015/0327947 | A1* | 11/2015 | Schoenefeld | A61B 17/15 606/87 |
| 2016/0143697 | A1 | 5/2016 | Chen | |
| 2016/0157751 | A1* | 6/2016 | Mahfouz | A61B 5/062 600/409 |
| 2017/0000566 | A1* | 1/2017 | Gordon | A61B 34/10 |
| 2017/0156799 | A1* | 6/2017 | Bozung | A61B 17/0218 |

FOREIGN PATENT DOCUMENTS

| | | |
|---|---|---|
| JP | 2006-519636 A | 8/2006 |
| JP | 2009-172124 A | 8/2009 |
| WO | 03/096920 A1 | 11/2003 |
| WO | 2004-071309 A1 | 8/2004 |
| WO | 2011/007806 A1 | 1/2011 |

OTHER PUBLICATIONS

Japanese Office Action dated Sep. 6, 2016 for Japanese Application No. 2015-522826.
International Search Report dated Sep. 10, 2014 for Application No. PCT/JP2014/065448 with an English translation.
J-PlatPat English abstract of JP 2009-172124 A.
J-PlatPat partial English translation of JP 2001-507614 A.

* cited by examiner

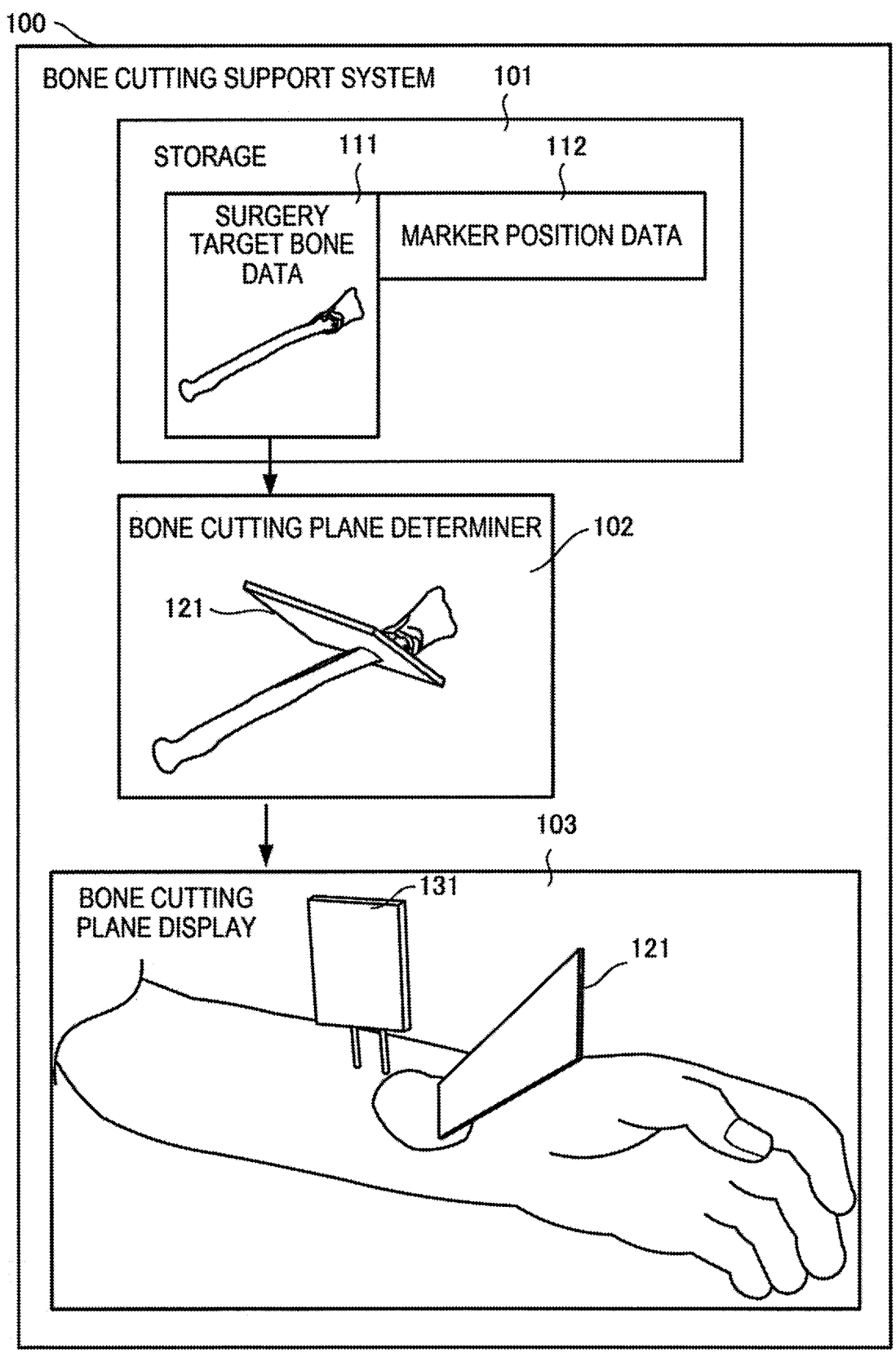
F I G. 1

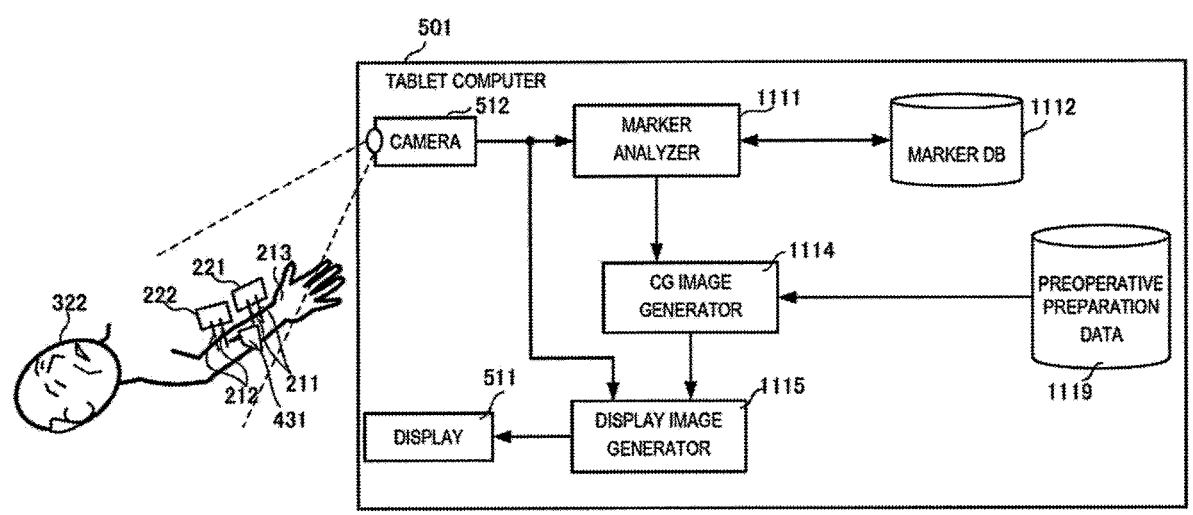
F I G. 11

1401

| FIRST TARGET BONE AND REFERENCE BONE ID | ANALYZED 3D POSITION DATA OF FIRST MARKER | STORED 3D POSITION DATA OF FIRST MARKER | COORDINATE-CONVERTED 3D DATA OF FIRST TARGET BONE | COORDINATE-CONVERTED 3D DATA OF REFERENCE BONE | 3D DATA OF BONE CUTTING PLANE |
|---|---|---|---|---|---|
| | | | | | |
| ⋮ | | | | | |

1411, 1412, 1413, 1414, 1415, 1416

F I G. 14

| SECOND TARGET BONE ID | ANALYZED 3D POSITION DATA OF SECOND MARKER | STORED 3D POSITION DATA OF SECOND MARKER | COORDINATE-CONVERTED 3D DATA OF SECOND TARGET BONE |
|---|---|---|---|
|  |  |  |  |
| ⋮ |  |  |  |

F I G. 15

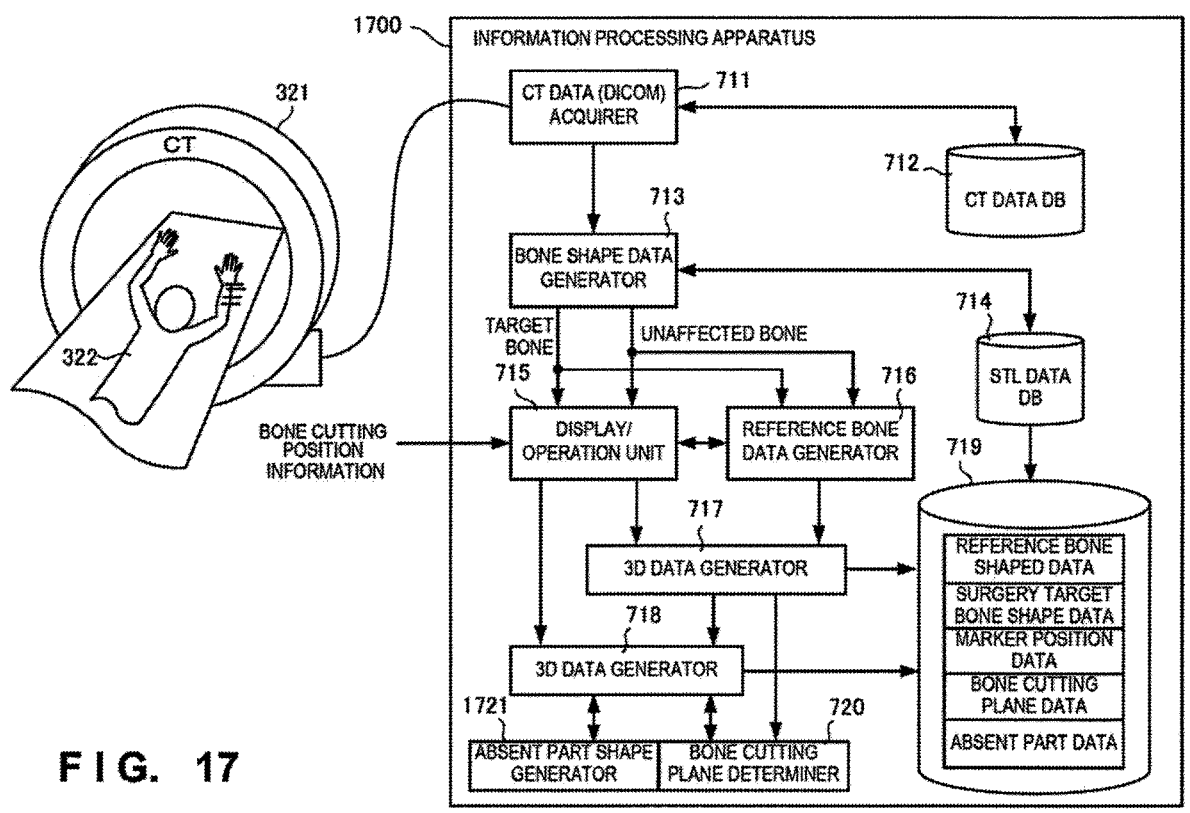
F I G. 17

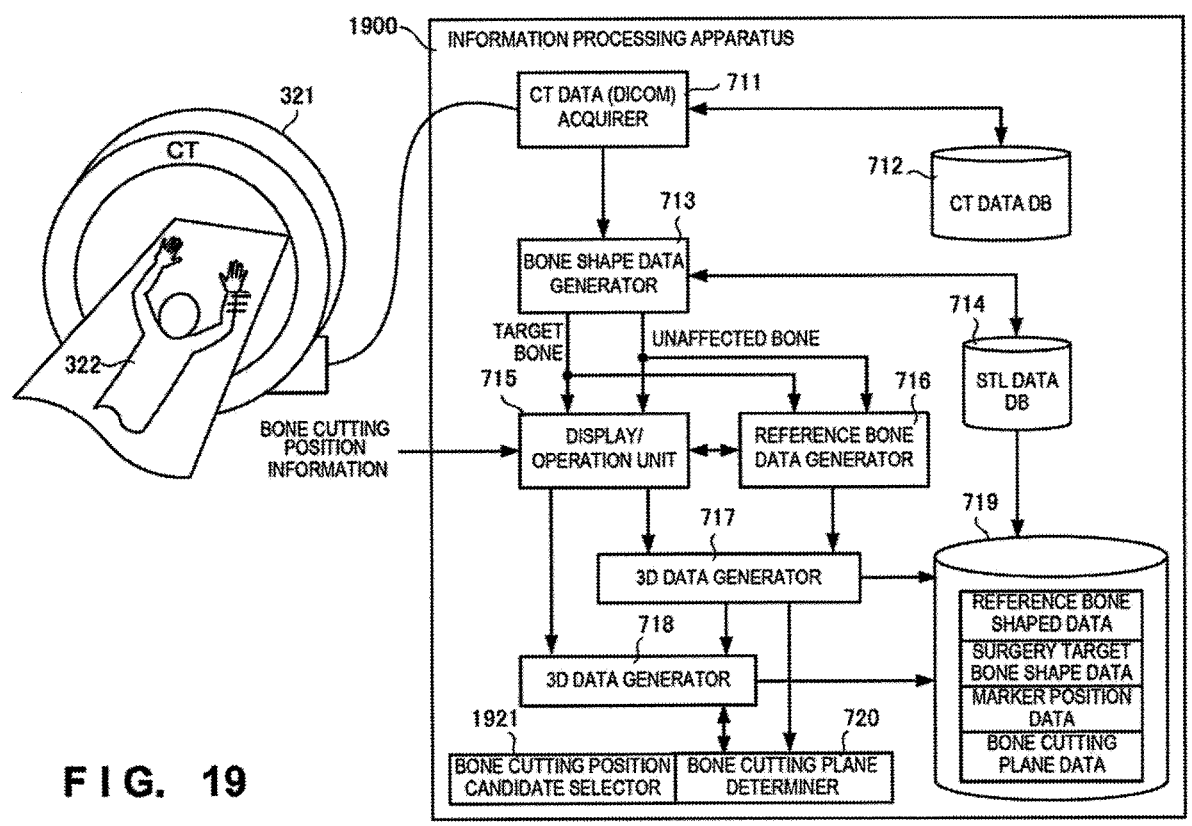
F I G. 19

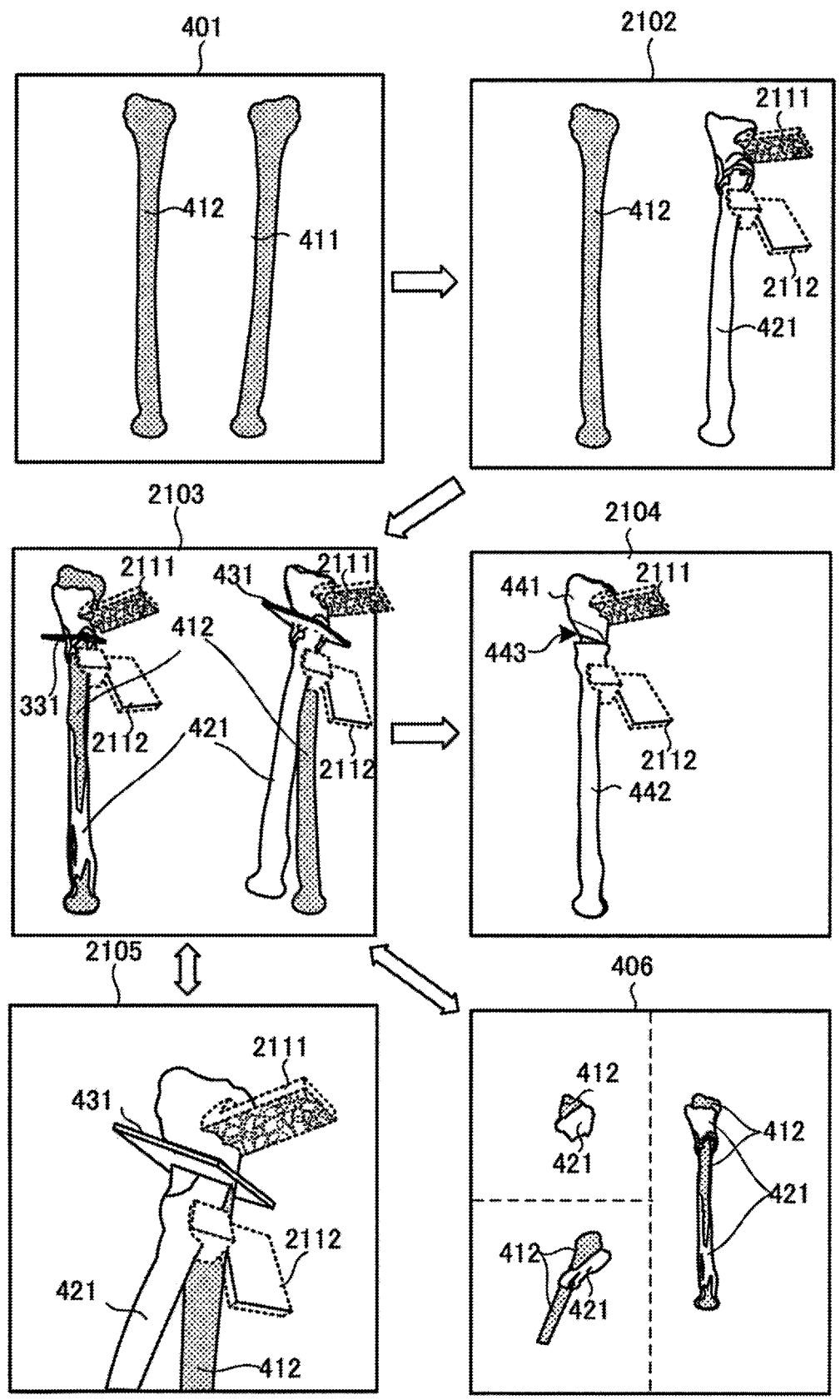
F I G. 21A

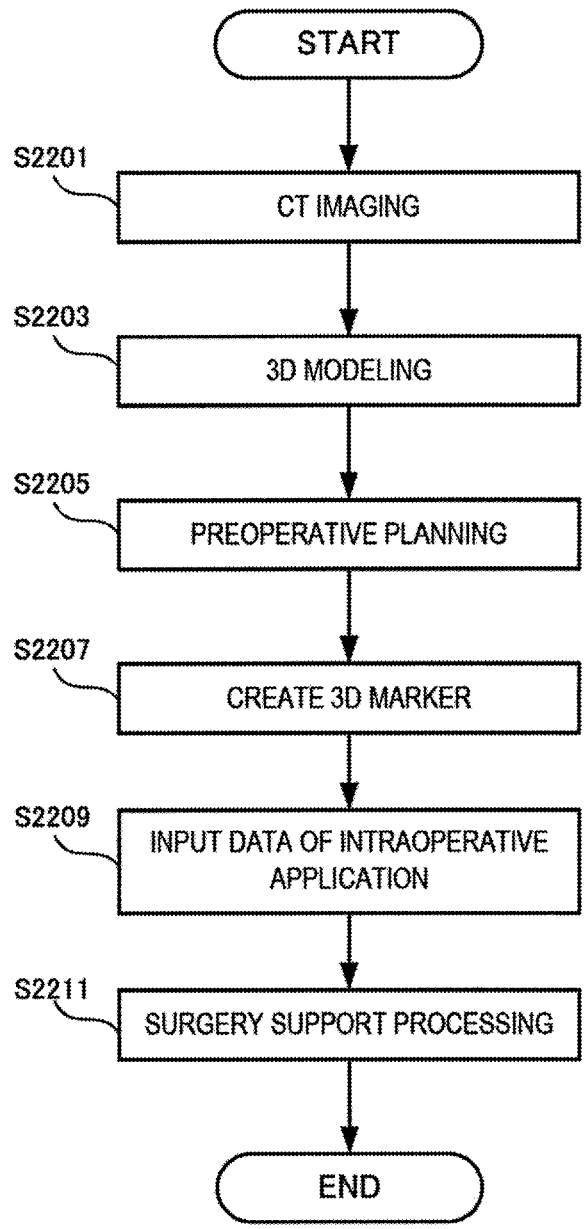
F I G. 22

| PATIENT NAME | AFFECTED PART | TECHNIQUE | PLANNING ITEM | 3D DATA |
|---|---|---|---|---|
| A | RIGHT ARM | MALUNION OF DISTAL RADIUS | 3D MARKER | 3D MARKER GENERATION DATA / MARKER PLACEMENT POSITION DATA |
| | | | BONE CUTTING PLANE | BONE CUTTING PLANE POSITION DATA |
| | | | ⋮ | |

F I G. 24

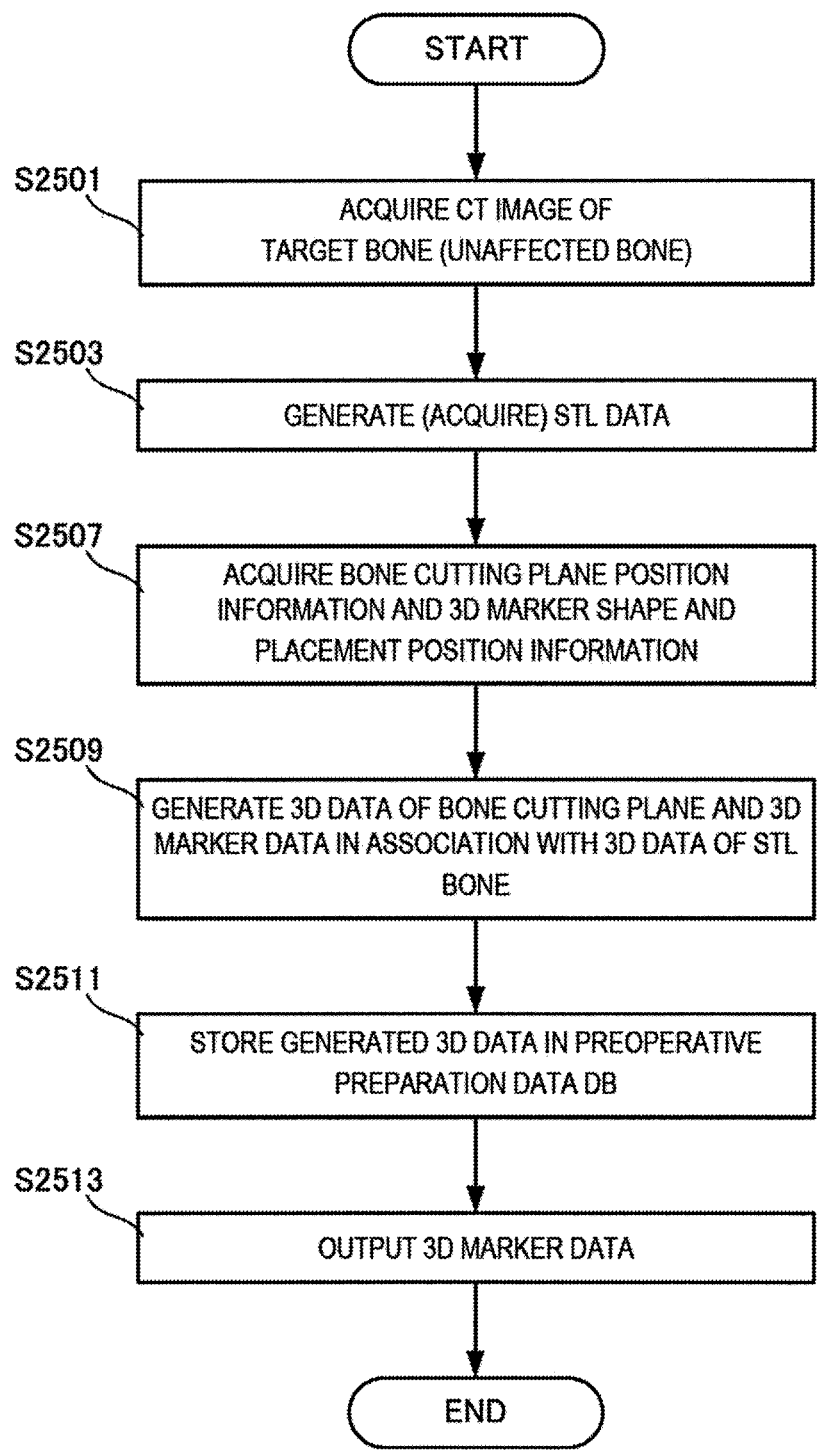
F I G. 25

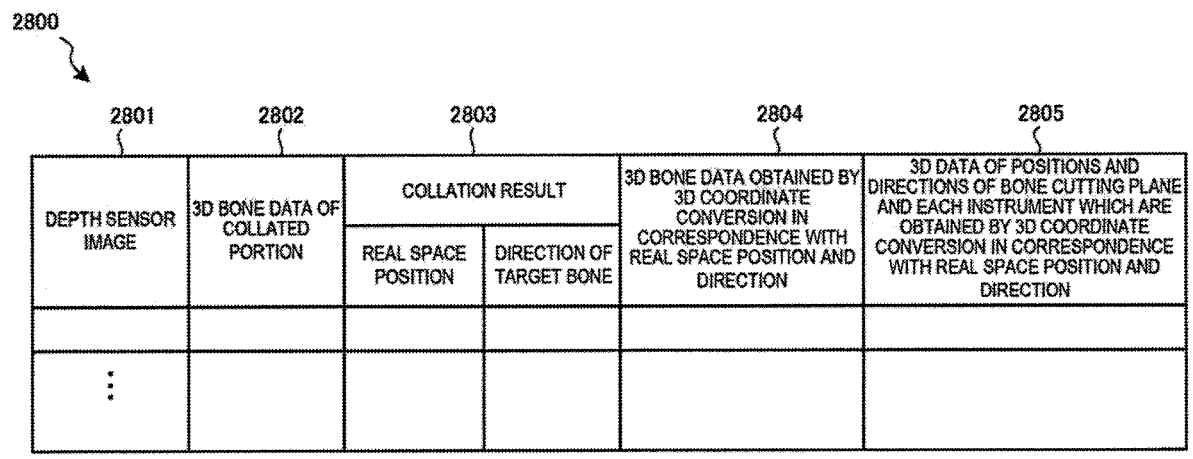
F I G. 28

BONE CUTTING SUPPORT SYSTEM, INFORMATION PROCESSING APPARATUS, IMAGE PROCESSING METHOD, AND IMAGE PROCESSING PROGRAM

RELATED APPLICATION

This application is a continuation of application Ser. No. 14/898,021 filed on Dec. 11, 2015, which is an application under 35 U.S.C. 371 of International Application No. PCT/JP2014/065448 filed on Jun. 11, 2014, the entire contents of each of which are incorporated herein by reference.

TECHNICAL FIELD

The present invention relates to a technique of supporting a surgical operation by image processing.

BACKGROUND ART

In the above-described technical field, patent literature 1 discloses a technique of determining a bone cutting position from an inverted image of an unaffected bone and an image of a target bone. Patent literature 2 discloses a technique of generating a prosthetic artificial bone model based on a determined bone cutting position. Non-patent literature 1 shows software that generates 3D bone surface model (STL: Stereo Lithography) data from DICOM (Digital Imaging and Communication in Medicine) data that is a standard format of a medical image of CT (Computed Tomography)/MRI (Magnetic Resonance Imaging) or the like. Non-patent literature 2 shows software that simulates bone and joint surgery in advance using 3D bone surface model (STL) data.

CITATION LIST

Patent Literature

Patent literature 1: Japanese Publication No. 2006-519636
Patent literature 2: International Publication No. WO2011/007806

Non-Patent Literature

Non-patent literature 1: Simple bone model 3D data creation software (BoneViewer), Company Report, Orthree Co. Ltd.
(http://www.orthree.jp/pdf/case_bv.pdf)
Non-patent literature 2: Bone and joint surgery simulation software (BoneSimulator), Company Report, Orthree Co. Ltd.
(http://www.orthree.jp/pdf/case_bs.pdf)

SUMMARY OF THE INVENTION

Technical Problem

However, the techniques described in the literatures above require expert knowledge and operations of a doctor to grasp the state of a bone after bone cutting. It is therefore necessary to depend on the doctor's experience to determine the bone cutting position or determine whether the bone cutting position is appropriate. Additionally, the bone cutting position during surgery needs to be determined by the doctor by observing the actual bone in the living body.

The present invention enables to provide a technique of solving the above-described problems.

Solution to Problem

One aspect of the present invention provides a bone cutting support system comprising:
a storage that stores 3D shape data of a surgery target bone and position data of a marker in association with each other;
a bone cutting plane determiner that determines, based on the 3D shape data of the surgery target bone, a position and direction of a bone cutting plane representing a plane to cut the surgery target bone; and
a bone cutting plane display that displays the determined bone cutting plane based on an image obtained by capturing the marker.

Another aspect of the present invention provides an information processing apparatus used in the cutting support system, comprising:
a storage that stores 3D shape data of a surgery target bone and position data of a marker in association with each other; and
a bone cutting plane determiner that determines, based on the 3D shape data of the surgery target bone, a position and direction of a bone cutting plane representing a plane to cut the surgery target bone.

Still other aspect of the present invention provides an image processing method used in the cutting support system, comprising:
storing 3D shape data of a surgery target bone and position data of a marker in association with each other; and
determining, based on the 3D shape data of the surgery target bone, a position and direction of a bone cutting plane representing a plane to cut the surgery target bone.

Yet another aspect of the present invention provides an image processing program used in the cutting support system, which causes a computer to execute a method comprising:
storing 3D shape data of a surgery target bone and position data of a marker in association with each other; and
determining, based on the 3D shape data of the surgery target bone, a position and direction of a bone cutting plane representing a plane to cut the surgery target bone.

Advantageous Effects of Invention

According to the present invention, it is possible to properly indicate a bone cutting plane determined in advance to a doctor during surgery.

BRIEF DESCRIPTION OF THE DRAWINGS

FIG. 1 is a block diagram showing the arrangement of a surgical operation support system according to the first embodiment of the present invention;

FIG. 11 is a block diagram showing the functional arrangement of a tablet computer in the intraoperative image processing system according to the second embodiment of the present invention;

FIG. 14 is a view showing the arrangement of an intraoperative image generation table used by a CG image generator according to the second embodiment of the present invention;

FIG. 15 is a view showing the arrangement of an intraoperative image generation table used by the CG image generator according to the second embodiment of the present invention;

FIG. 17 is a block diagram showing the functional arrangement of an information processing apparatus according to the third embodiment of the present invention;

FIG. 19 is a block diagram showing the functional arrangement of an information processing apparatus according to the fourth embodiment of the present invention;

FIG. 21A is a view for explaining the outline of preoperative preparation data generation processing using an information processing apparatus according to the fifth embodiment of the present invention;

FIG. 22 is a flowchart showing the processing procedure of an entire surgical operation support system including a preoperative preparation data generation system and an intraoperative image processing system according to the fifth embodiment of the present invention;

FIG. 24 is a view showing the arrangement of a preoperative preparation data DB according to the fifth embodiment of the present invention;

FIG. 25 is a flowchart showing the procedure of bone cutting plane generation processing according to the fifth embodiment of the present invention;

FIG. 28 is a view showing a data table used by a bone surface image collator according to the sixth embodiment of the present invention.

DESCRIPTION OF THE EMBODIMENTS

Figure 2:
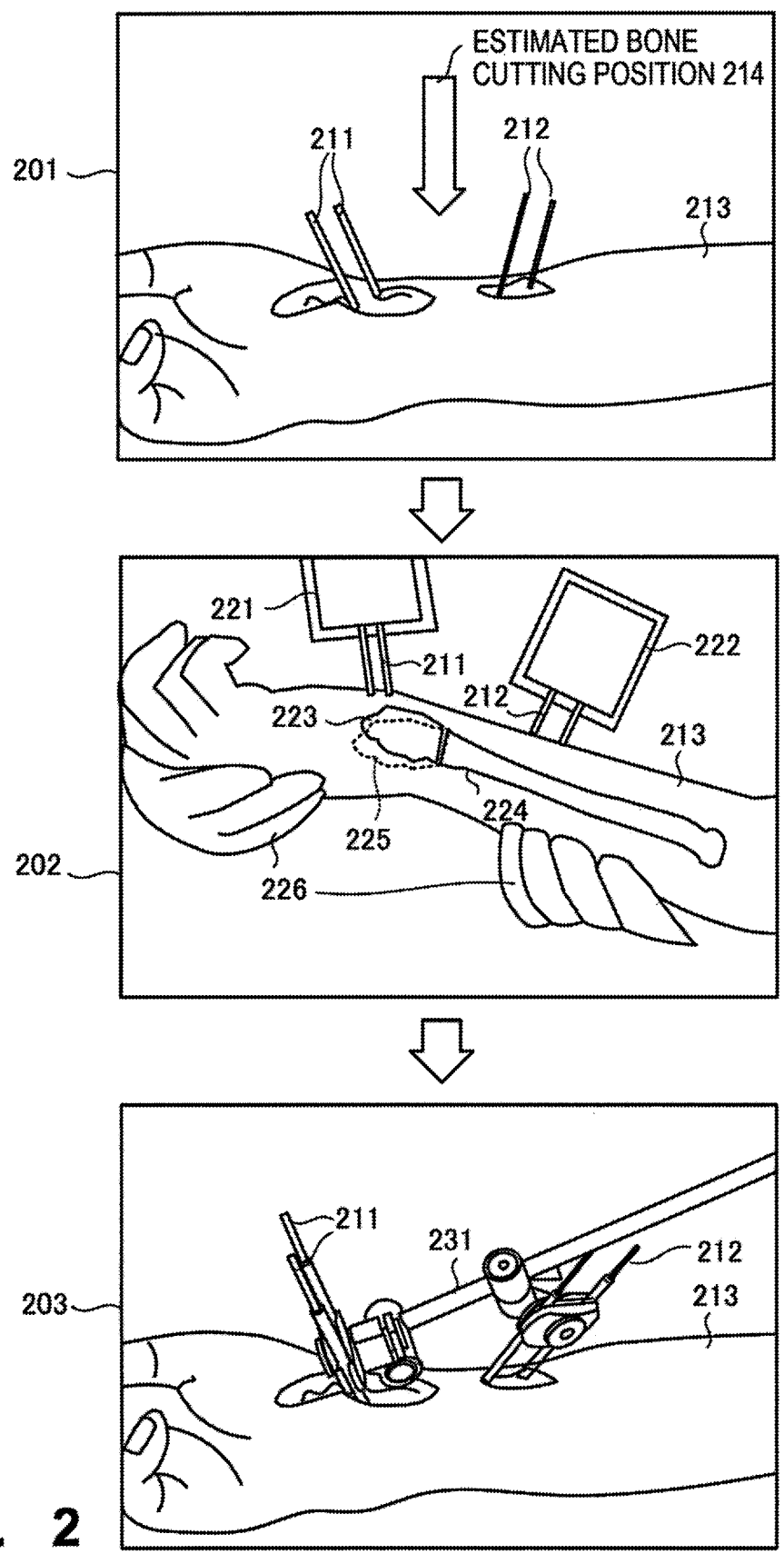
FIG. 2 is a view for explaining the outline of an entire surgical operation according to the second embodiment of the present invention.

Preferred embodiments of the present invention will now be described in detail with reference to the drawings. It should be noted that the relative arrangement of the components, the numerical expressions and numerical values set forth in these embodiments do not limit the scope of the present invention unless it is specifically stated otherwise.

Note that the word "move" is used in this specification to express, on a 2D display screen, "rotational movement" and/or "translation" of an image in a 3D space.

First Embodiment

A bone cutting support system 100 according to the first embodiment of the present invention will be described with reference to FIG. 1. The bone cutting support system 100 is a system that supports osteotomy by image processing.

As shown in FIG. 1, the bone cutting support system 100 includes a storage 101, a bone cutting plane determiner 102, and a bone cutting plane display 103. The storage 101 stores 3D shape data 111 of a surgery target bone in association with position data 112 of a marker fixed to the surgery target bone. On the other hand, the bone cutting plane determiner 102 determines the position and direction of a bone cutting plane or a bone cutting guide plane 121 representing a plane to guide for cutting the surgery target bone based on the 3D shape data 111 of the surgery target bone. The bone cutting plane display 103 displays the determined bone cutting plane 121 based on an image obtained by capturing a marker 131 fixed to the surgery target bone.

According to this embodiment, it is possible to properly indicate a bone cutting plane determined in advance to a doctor during surgery.

Second Embodiment

A surgical operation support system according to the second embodiment of the present invention will be described next. The surgical operation support system according to this embodiment generates 3D data of a first target bone that is a part of a surgery target bone serving as the reference of the disposition of the surgery target bone and 3D data of a reference bone serving as the reference of the shape after healing in advance, and stores the data in association with a first marker (for example, a 2D code) fixed to the first target bone. The surgical operation support system also generates 3D data of a second target bone that is the other part of the surgery target bone, and stores the data in association with a second marker (for example, a 2D code) fixed to the second target bone. In surgery, a bone cutting plane and the 3D positions of the first target bone and the second target bone are determined from the captured first and second markers using the AR (Augmented reality) technology and displayed based on the stored 3D data. It is determined whether the second target bone and the reference bone adequately overlap, thereby determining an appropriate disposition of the surgery target bone. This processing supports determining an appropriate disposition of the surgery target bone by a doctor.

The outline of the arrangement and processing of the surgical operation support system according to this embodiment will be described below with reference to FIGS. 2 to 7. The surgical operation support system is roughly divided into a preoperative preparation data generation system and an intraoperative image processing system. The preoperative preparation data generation system is a system that generates and displays 3D data of a first target bone, a second target bone, and a reference bone before surgery, and generates and stores data to be used during surgery. The intraoperative image processing system is a system that generates and displays a target bone image and a reference bone image based on marker image capturing, and supports determination of the disposition of the surgery target bone. However, the preoperative preparation data generation system and the intraoperative image processing system may be formed as one integrated system.

(Outline of Surgical Operation)

FIG. 2 is a view for explaining the outline of a whole surgical operation according to this embodiment. FIG. 2 shows an example of corrective osteotomy of an affected bone (surgery target bone) with malunion. The corrective osteotomy includes a preparation stage 201, a surgery target bone alignment stage 202, and a surgery target bone position fixing stage 203. In this embodiment, malunion surgery of a distal radius will be described as an example. However, the present invention is not limited to this, and is also applicable to malunion of another part or another bone or fracture treatment surgery.

In the preparation stage 201, pairs of pins 211 and 212 are fixed as support members for two markers at two points sandwiching an estimated bone cutting position 214 of the surgery target bone of a forearm 213 at a predetermined interval (for example, an interval of 1 cm or 2 cm). Portions having a sufficient strength and sectional area and capable of fixing two pins in the longitudinal direction of the surgery target bone are preferable as positions to insert and fix the pins. A length of about 5 cm to 10 cm suffices as a pin length that enables to set markers outside the forearm and easily capture them, although the length changes depending on the affected portion or bone. CT (Computed Tomography) imaging is performed in a state in which the pins 211 and 212 are fixed, thereby generating and storing 3D data of the surgery target bone with the pins. In addition, the positions and directions of markers to be fixed to the pins 211 and 212 later are set, and the position data of the markers, the 3D data of the surgery target bone, and the 3D data of the reference bone are associated with each other.

For example, the 3D data of pins included in the 3D data of the surgery target bone may be displayed, and the user may be caused to designate the proximal and distal end positions of the two pins using a pointing device or the like to define the position and direction of the marker to be attached to the pins. The relationship between a plane formed by the two pins and the position and direction of the marker may be set in advance or selected from a plurality of relationships (for example, the marker is parallel or perpendicular to the plane formed by the two pins, or makes an angle of 45° with respect to the plane). Alternatively, for example, 3D shape data of the pins themselves or one or a plurality of jigs to be used to fix the marker to the pins may be prepared. Then, the jigs may be attached in a 3D space to 3D data of the pins acquired by CT imaging to define the position of the marker. The relationship between the position and direction of the marker and the positions and directions of the surgery target bone and the reference bone is thus stored in a database.

Marker position data is data representing the relative positions of the position of the marker and the position of the surgery target bone. It need only be data representing the position of the marker viewed from the origin of the 3D space including the 3D data of the surgery target bone. The bone cutting plane data includes the relative position to the 3D data of the surgery target bone. For this reason, the relative relationship between the position of the marker and the position of the bone cutting plane in the same 3D space is consequently defined. That is, a position, size, and direction to display the bone cutting plane can be determined from the position, size, and direction of the marker in the captured image by referring to this database.

During surgery, the affected part is cut open, and bone cutting is carried out at the position indicated by the system. After that, in the surgery target bone alignment stage 202, markers 221 and 222 are shot. The positions, sizes, and directions of the markers 221 and 222 are recognized from the captured image, and a database is referred to, thereby deriving the positions, sizes, and directions of surgery target bones. Surgery target bones 223 and 224 of the derived positions, sizes, and directions and a reference bone 225 are displayed.

When the doctor holds the forearm 213 of the patient by a hand 226 and bends or twists the arm, the state of the marker 221 in the captured image changes. The surgery target bone 223 in the displayed image is displayed such that its display position, size, and tilt change in accordance with the change in the position, size, and tilt of the marker 221. On the other hand, 3D shape data of a reference bone 225 is stored in advance together with the relative relationship to the position, size, and tilt of the marker 222. When the marker 222 is captured, the reference bone 225 is displayed at a predetermined position. When the doctor finds a position at which the surgery target bone 223 overlaps the reference bone 225, the process advances to the surgery target bone position fixing stage 203.

In the surgery target bone position fixing stage 203, to maintain the determined appropriate relative disposition of the surgery target bones 223 and 224 in the forearm 213 of the patient, the pins 211 and 212 at the position at which the surgery target bone 223 overlaps the reference bone 225 are fixed by a fixing tool 231.

With the support by the surgical operation support system, it is possible to make the incision part small and speed up the surgery.

(Other Marker Fixing Methods)

In FIG. 2, the pins 211 and 212 project outside the wound. However, the present invention is not limited to this. For example, pins that are short (1 to 2 cm) enough to put their distal ends within the wound may be used. During surgery (alignment stage 202), long pins may newly be connected to the short pins, and the markers 221 and 222 may then be attached. Alternatively, only a bone may be captured by CT imaging without inserting pins, and virtual pins may be inserted into the thus generated CG data of the bone. After that, a wound may be opened during surgery, and actual pins may be inserted to the position as in the CG data. At this time, the position of a marker may be determined using the CG data of the bone with the virtual pins. A pattern (pattern with pins) that exactly fits on the bone of the affected part may be formed by a 3D printer, and pins may be inserted based on the pattern, thereby inserting actual pins to the same position as in the CG data. The marker may be attached to the pattern itself in a state in which the pattern is exactly fitted on the bone. Feature points of the bone captured by the digital camera may be discriminated and overlaid on the CG data with pins, thereby inserting the pins to the same position in the same direction as in the CG data. These methods can suppress the burden on the patient and establishment of an infectious disease after CT imaging with the pins being inserted.

(Arrangement of Preoperative Preparation Data Generation System)

Figure 3:
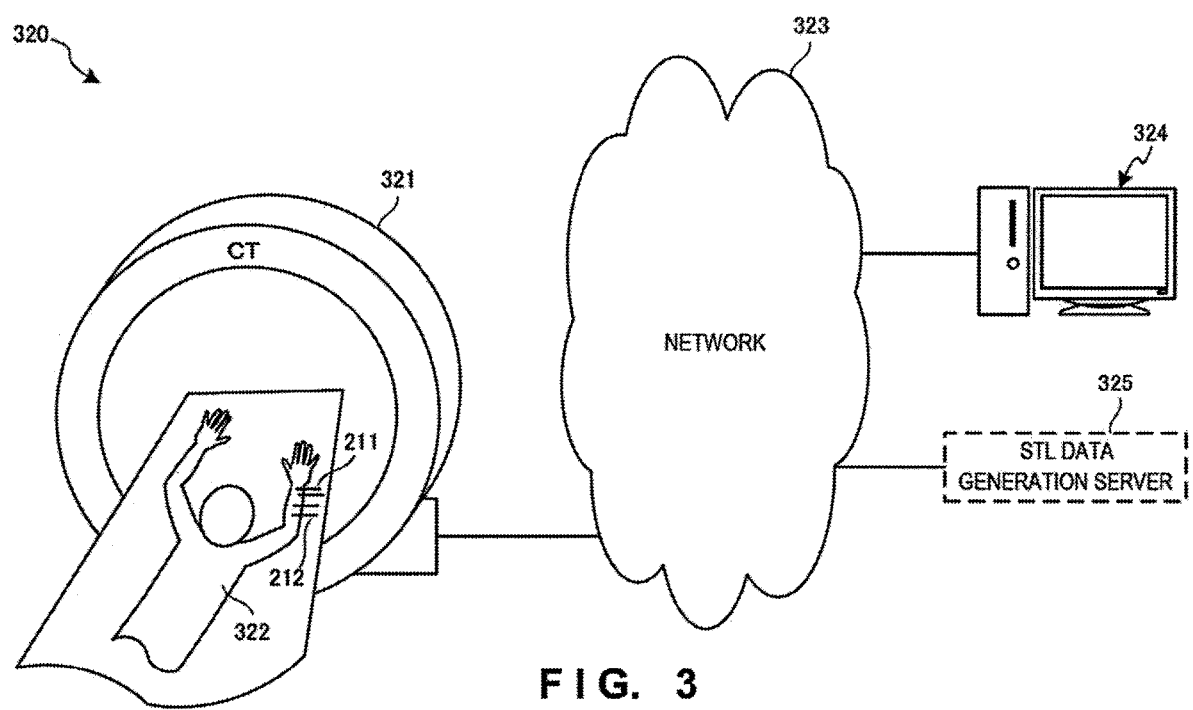
FIG. 3 is a view showing the arrangement of a preoperative preparation data generation system according to the second embodiment of the present invention.

FIG. 3 is a view showing the arrangement of a preoperative preparation data generation system 320.

The preoperative preparation data generation system 320 includes an information processing apparatus 324 configured to generate a reference image, and a CT scanner 321 that acquires a tomographic image of a patient 322, which are connected via a network 323. The preoperative preparation data generation system 320 may also include, as an option, an STL data generation server 325 that generates 3D bone surface data (STL data) from tomographic image data. Note that the network can be either a WAN or a LAN.

In this embodiment, tomographic images of the affected part of the patient 322 and a part serving as the reference of the affected part are acquired by the CT scanner 321. In this example, for example, tomographic images of the right forearm in which four pins are inserted and fixed in the surgery target bone and tomographic images of the left forearm on the unaffected side are acquired. The tomographic image data are sent to the information processing apparatus 324 via the network 323 and converted into 3D data by the information processing apparatus 324. Note that the conversion from tomographic image data to 3D data may be done by the STL data generation server 325.

Note that living body data used in this embodiment is not limited to data acquired by CT/MRI, and 3D data is not limited to STL data.

(Preoperative Preparation Data Generation Processing)

Figure 4:
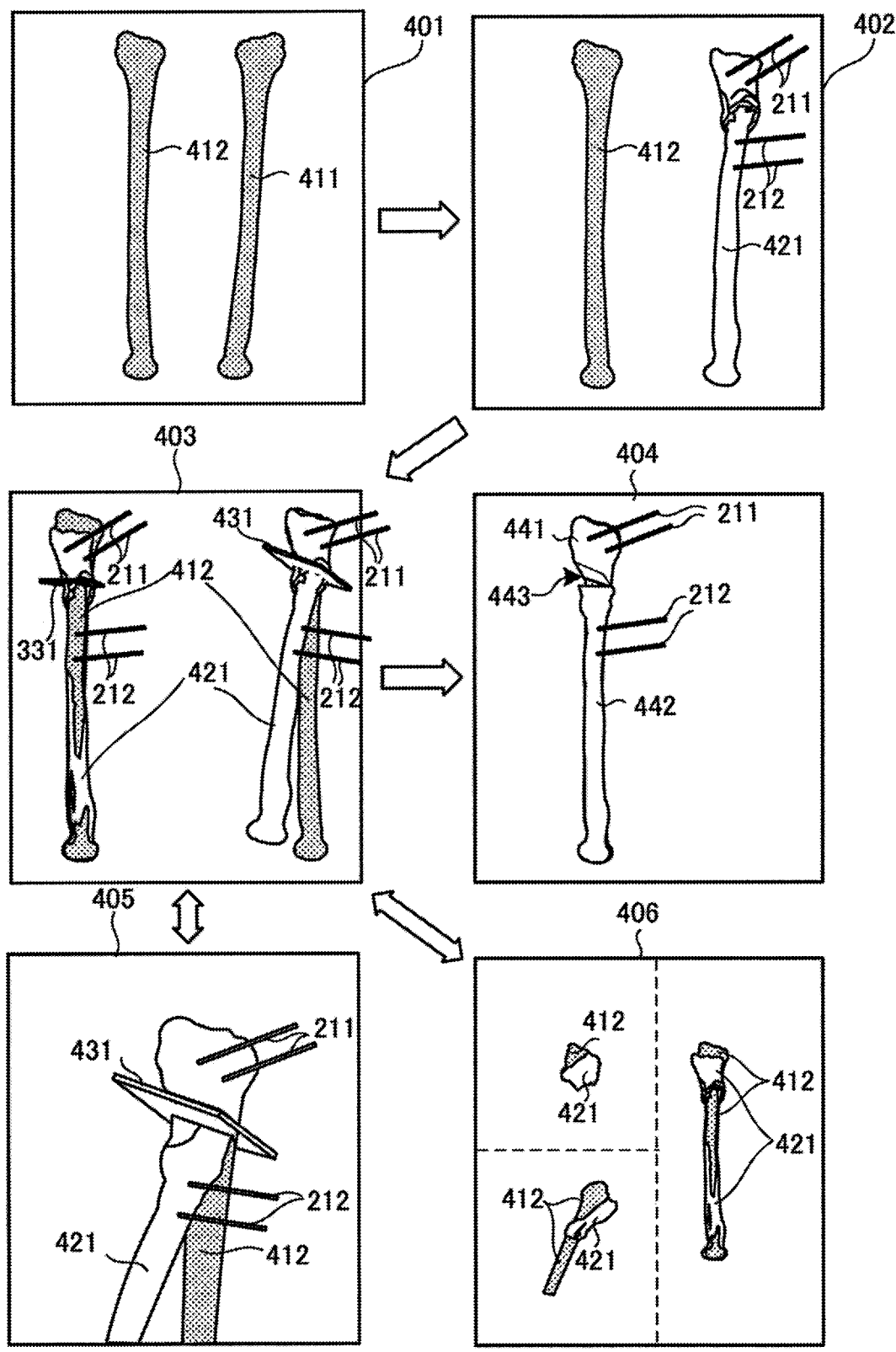
FIG. 4 is a view for explaining the outline of preoperative preparation data generation processing using an information processing apparatus according to the second embodiment of the present invention.

FIG. 4 is a view for explaining the outline of preoperative preparation image generation processing using the information processing apparatus 324. Images 401 to 406 are CG (Computer Graphics) images displayed on the display screen of the information processing apparatus 324, which correspond to the stages of the preoperative preparation data generation processing, respectively.

In the first stage, as indicated by the image 401, an unaffected bone at a position (on the unaffected side) bilaterally symmetrical to the surgery target bone of the forearm 213 is internally captured by CT, MRI or the like. Thus generated 3D data 411 of the unaffected bone is inverted to generate mirror image data. Accordingly, 3D data (to be referred to as a reference bone hereinafter) 412 of a reference bone having the same shape as (at least partially overlapping) the surgery target bone is generated. Note that the reference bone image 412 is not limited to the mirror image data of the position unaffected bone on the unaffected side. For example, another bone of the patient with a similar shape, a radius of another patient, or a radius generated by CG may be used.

In the second stage, as indicated by the image 402, the surgery target bone of the forearm 213 is internally captured by CT scan or the like, and thus generated 3D data (to be referred to as a surgery target bone hereinafter) 421 of the surgery target bone (affected bone) is displayed. The surgery target bone 421 is generated from STL data captured in a state in which the pins 211 and 212 are fixed, and therefore includes the pins 211 and 212 even in the 3D data. The reference bone image 412 and the surgery target bone 421 are compared on the display screen, and the state of the surgery target bone 421 is confirmed.

In the third stage, the surgery target bone 421 is manipulated on the image 403 while referring to the enlarged display image 405 in which the observation point in the 3D space is moved close to the surgery target bone or the divided display image 406 in which a plurality of images from different observation points (in this example, images from three directions) are simultaneously displayed. That is, the surgery target bone 421 is moved and rotated with respect to the reference bone image 412 to overlay the end portions of the reference bone image 412 on the end portions of the surgery target bone 421.

If the bone cutting plane can be estimated to exist on the upper end side, first, the lower ends of the surgery target bone 421 and the reference bone image 412 are overlaid to determine the bone cutting plane of the surgery target bone 421, as shown on the left side. In particular, the shapes (feature points) of the joint portions (the lower ends or upper ends in the drawing) are overlaid to recognize the distortion, bending, or deformation of the surgery target bone 421. Then, the bone is compared with the reference bone gradually upward from the lower end, and a branch position where deviation from the reference bone starts is determined as a bone cutting plane image 431. Here, the bone cutting plane image 431 is a rectangular plane having a predetermined shape and size. However, the present invention is not limited to this. A plane including a curved plane may be used in accordance with the purpose of bone cutting.

Note that the doctor may evaluate and determine the bone cutting plane image 431 while observing the overlay state between the reference bone image 412 and the surgery target bone 421. However, an optimum bone cutting plane may be obtained by calculation. For example, the lower ends are overlaid, and a non-overlay volume per unit length in the axial direction between the surgery target bone 421 and the reference bone image 412 is calculated sequentially from the lower end. Uppermost points at which the non-overlay volume does not exceed a predetermined value may be connected to form a plane serving as the bone cutting plane image 431. Alternatively, the surface of the reference bone image 412 may finely be divided into unit areas, and positions at which the distance in the vertical direction up to the surface of the surgery target bone 421 exceeds a predetermined value on a unit area basis may be connected to automatically derive the bone cutting plane image 431. Otherwise, when two target bone images 441 and 442 generated by bone cutting are overlaid on the upper and lower ends of the reference bone image 412, as indicated by the image 404, the bone cutting plane may be determined such that the sum of volumes outside the reference bone image 412 (or the distances between the surfaces) is minimized. Alternatively, when the two target bone images 441 and 442 generated by bone cutting are overlaid on the upper and lower ends of the reference bone image 412, as indicated by the image 404, the bone cutting plane may be determined such that a gap (absent part) 443 between the separated bones of the target bone images 441 and 442 is minimized. At any rate, the position and angle of an optimum bone cutting plane can be obtained by repeating a simulation using a plane of every direction as a bone cutting plane candidate while shifting the position by a unit distance (for example, 1 mm) in the axial direction of the surgery target bone 421. On, for example, a radius, for example, 300×24× 72=about 500,000 planes are obtained as bone cutting plane candidates within the range of 60° to −60° with respect to a plane perpendicular to the bone axis in steps of 5°×5°.

When the bone cutting plane image 431 is thus determined, in the fourth stage, the 3D data of the two target bone images 441 and 442 obtained by separating the surgery target bone 421 by the bone cutting plane image 431 are generated and stored. That is, the set of the target bone image 442 and the reference bone image 412 which are overlaid is stored in association with the marker 222 attached to the pins 212. As indicated by the image 404, the target position of the target bone image 441 with respect to the target bone image 442 or the reference bone image 412 is stored in association with the position data of the marker 221 attached to the pins 211. Accordingly, if the position or tilt of the marker 221 can be recognized in the real space, the target position or tilt of the target bone image 441 can be estimated.

Furthermore, the data of the position, shape, and tilt of the bone cutting plane image 431 are stored in association with the position data of the marker 221 or 222. The position and direction of the marker 221 with respect to the pins 211 and the position and direction of the marker with respect to the pins 212 may be determined to one pattern in advance. In this embodiment, the position and direction can be selected from a plurality of (for example, four) patterns. In a first marker attachment type, a marker is attached to be parallel to the pin plane formed by the two pins. In a second marker attachment type, a marker is attached to a plane that is parallel to the axial direction of the pins and perpendicular to the pin plane. In a third marker attachment type, a marker is attached to a plane that is parallel to the axial direction of the pins and makes an angle of 45° with respect to the pin plane. In a fourth marker attachment type, a marker is attached to a plane that is parallel to the axial direction of the pins and makes an angle of 135° with respect to the pin plane. Alternatively, a marker may be attached to a plane perpendicular to the axial direction of the pins. The relative positional relationship between a marker and a surgery target bone or reference bone to be displayed is changed in accordance with how the marker is attached to the actual pins.

By using the thus prepared data, display of the target bone image 441 and the reference bone image 412, display of the target bone image 442, and display of the bone cutting plane image 431 can be performed based on the positions, sizes, and directions of the markers captured in surgery. Note that the gap 443 between the target bone image 441 and the target bone image 442 represents the shape of a connecting bone necessary in surgery. Hence, the 3D shape of the connecting bone necessary in surgery can also be acquired at this time.

Note that in surgery, the combination of the target bone images 441 and 442 determined as the target disposition on the image 404 may integrally be used and displayed without using the reference bone image 412 generated from the unaffected side. In this case, the positions of the pins 211 and 212 serving as the support members of the first and second markers 221 and 223 in a state in which both of the target bone images 441 and 442 are overlaid on the reference bone image 412 are stored in the storage as target relative position data. The target positions of the pins 212 of the second marker 222 are displayed based on the stored target relative position data.

In this embodiment, since corrective osteotomy of an affected bone (surgery target bone) with malunion is carried out, target bones on both sides of the bone cutting plane are taken into consideration. However, the present invention is not limited to this. For example, in artificial joint transplant surgery, bone cutting planes (for example, three planes) used to generate planes to which an artificial joint is to be attached are displayed using the above-described AR technology, thereby implementing accurate bone cutting. For example, 3D CG models of artificial joints in three sizes S, M, and L are prepared. When healing osteoarthritis, the unaffected bone is CT-scanned, and each artificial joint model is overlaid on the 3D data of the surgery target bone in a 3D virtual space. The relative positional relationship between a marker and the bonding surface of the artificial joint model is stored, and a blade model is AR-displayed according to the bonding surface during surgery. A blade representing the bone cutting plane may be pasted to the 3D model of the artificial joint. In this case, one marker suffices. Note that a marker may be attached to an actual blade, the marker position may be recognized, and movement of the blade to the target position may be instructed.

(Arrangement of Intraoperative Image Processing System)

Figure 5:
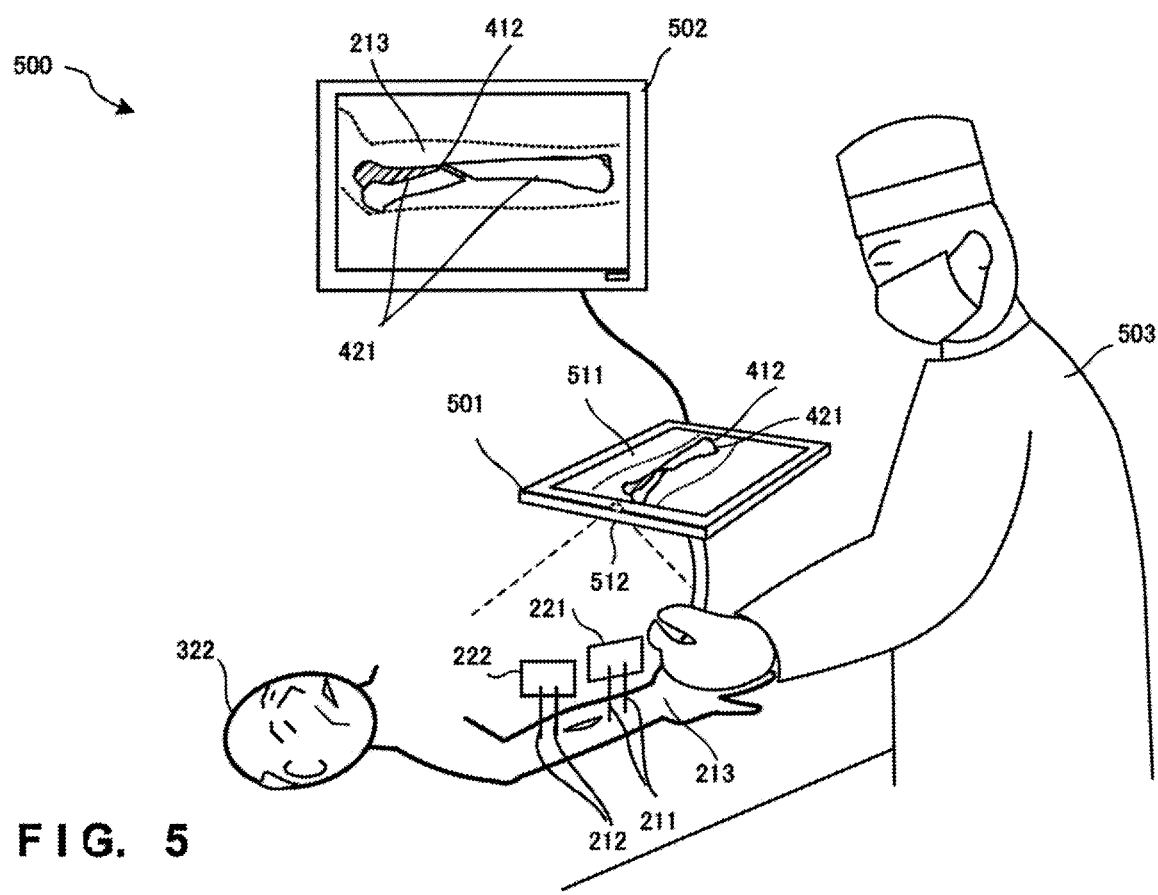
FIG. 5 is a view showing the schematic arrangement of an intraoperative image processing system according to the second embodiment of the present invention.

FIG. 5 is a view showing the schematic arrangement of an intraoperative image processing system 500 according to this embodiment. The intraoperative image processing system 500 includes a tablet computer 501 as an information processing apparatus, and a display device 502. The tablet computer 501 includes a display 511 and a camera 512 (digital camera).

The tablet computer 501 is fixed at a position at which the display 511 faces a doctor 503, and the camera 512 faces the markers 221 and 222. The tablet computer 501 stores the 3D data of the surgery target bone in advance, and recognizes the position and direction of the surgery target bone from the images of the markers 221 and 222. The tablet computer 501 displays the image of an ideal bone cutting plane at the recognized position on the display 511. Accordingly, the doctor 503 can grasp the bone cutting plane at a glance.

In addition, when the doctor 503 holds the forearm 213 of the patient 322 and twists or stretches it, the positions of the markers 221 and 222 change accordingly. Hence, the surgery target bone 421 in the display 511 also moves or rotates. The forearm 213 is moved in this way to overlay the target bone image 442 in the display 511 on the reference bone image 412, thereby determining the target position of the surgery target bone. The pins 211 and 212 are fixed at the determined position using the fixing tool 231.

(Intraoperative Target Bone Alignment Processing)

Figure 6A:
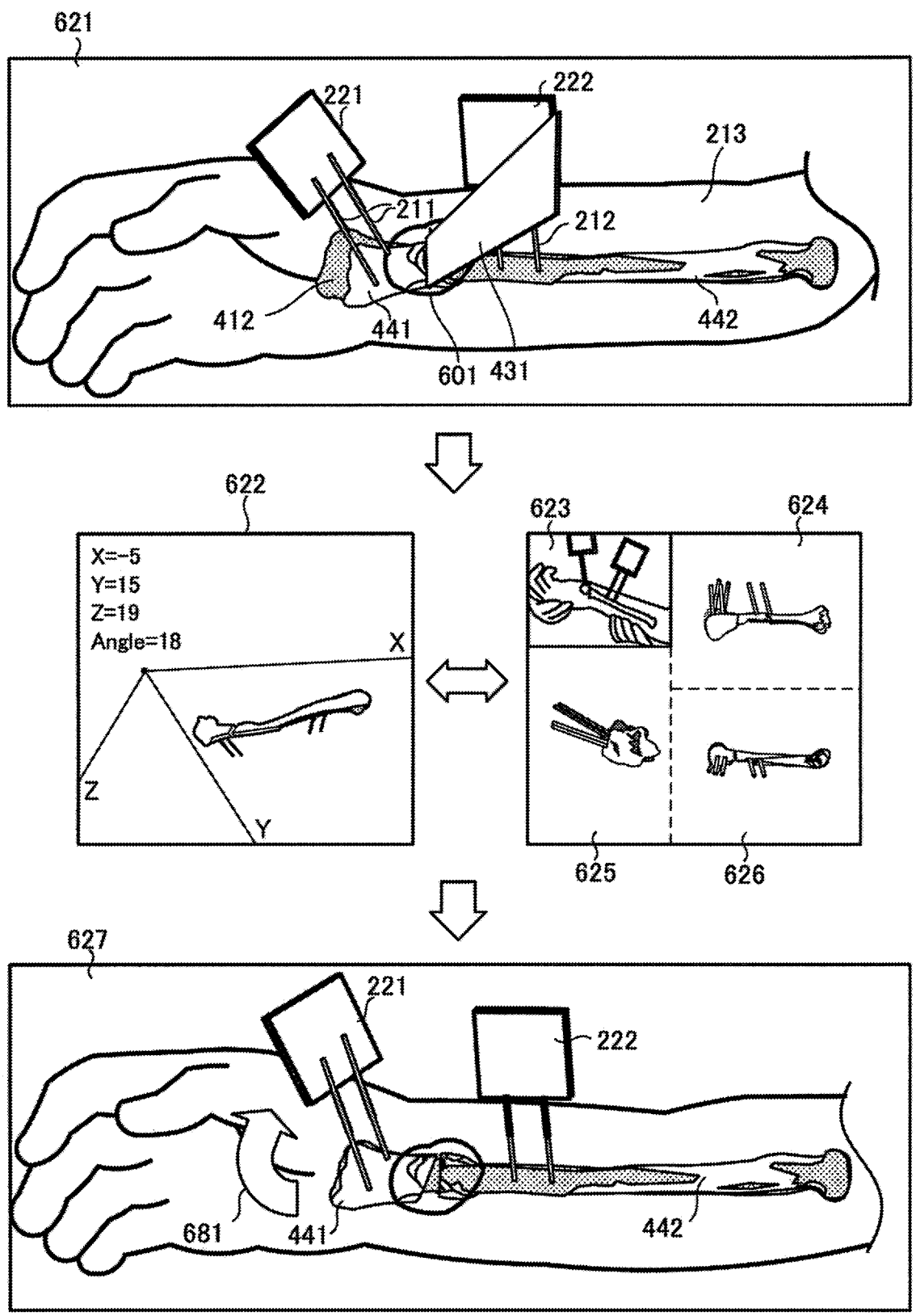
FIG. 6A is a screen transition diagram for explaining the outline of a bone cutting operation and alignment operation of a surgery target bone during surgery according to the second embodiment of the present invention.

FIG. 6A is a screen transition diagram for explaining the outline of a bone cutting operation and alignment operation of the surgery target bone during surgery. Before surgery, the markers 221 and 222 are fixed to the pins 211 and 212.

In a bone cutting stage, the bone cutting plane image 431 is three-dimensionally displayed on the display 511, like an image 621, and the surgery target bone is cut at an appropriate position. In the image 621, a thick line indicates an image captured by the camera 512, and a thin line indicates a CG image generated from 3D data.

The doctor inserts a bone cutting blade into the affected part according to the bone cutting plane image 431 and separates the affected bone with malunion. The doctor then manipulates the target bone image 441 with respect to the target bone image 442 by moving the forearm of the patient while referring to an image 622 of a coordinate space or divisionally displayed images 623 to 626. In the images 621 to 626, the target bone images 441 and 442 of positions, sizes, and directions according to the positions, sizes, and directions of the markers 221 and 222 obtained by image capturing are displayed.

The image 622 displays the angles between the observation point and the X-axis, Y-axis, and Z-axis of the 3D space. The relative positions of the reference bone image 412 and the target bone images 441 and 442 in the 3D space are extracted and displayed. The images of the target bone images 441 and 442 can be rotated on the screen by moving the observation point. The images 623 to 626 are divisionally displayed images displayed on one screen. The image 623 is the overlay image of the captured image and the CG image, like the image 621. The image 624 corresponds to only the CG image extracted from the image 623, and displays the reference bone and the target bone with the pins. The image 625 is the image of the reference bone image 412 and the target bone images 441 and 442 viewed from the axial direction of the bones, which makes an angle of 90° with respect to the camera 512. The image 626 is the image of the reference bone image 412 and the target bone images 441 and 442 viewed from the pin insertion direction which makes an angle of 90° with respect to the camera 512. That is, the images 624 to 626 are three display images with observation points in the three axial directions of the 3D space. The doctor determines an appropriate disposition of the target bone images 441 and 442 while observing these display-screens.

An image 627 shows a state in which the target bone image 441 is overlaid on the reference bone image 412. In this state, the pins 211 and 212 attached to the target bone images 441 and 442 are fixed by the fixing tool.

(Outline of Intraoperative Bone Cutting Support Processing)

Figure 6B:
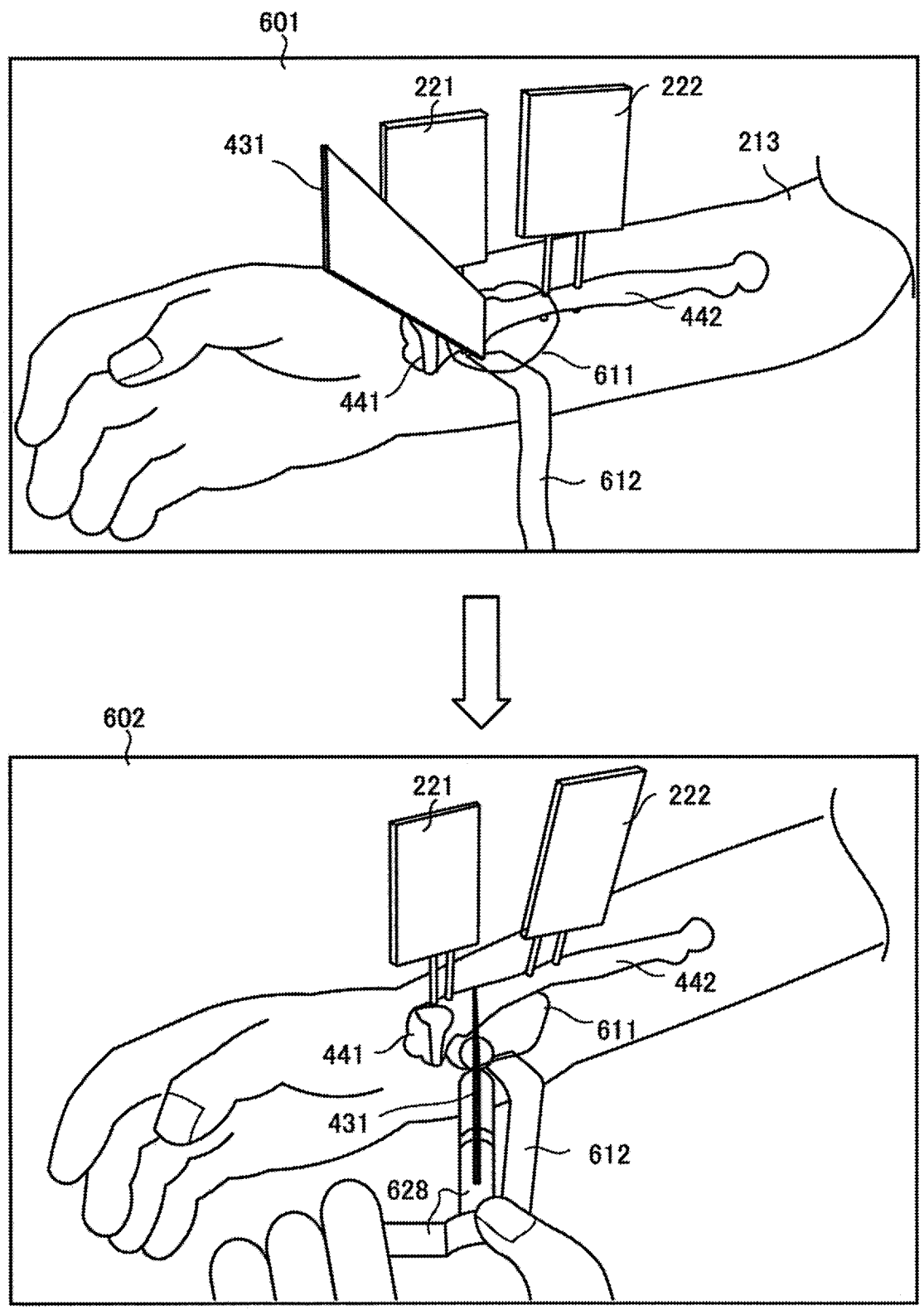
FIG. 6B is a view for explaining the outline of bone cutting support processing during surgery according to the second embodiment of the present invention.

FIG. 6B is a view for explaining the outline of bone cutting support processing during surgery according to this embodiment.

A display screen 601 displays the affected part (the forearm portion of the left hand) 213 with a forearm radius as a surgery target bone in the living body, and the markers 221 and 222 fixed to the divided surgery target bones, respectively, which are captured by the camera 512. The display screen 601 also displays an incision part 611 for bone cutting, and a holding instrument 612 that holds the incision part 611 in an open state for bone cutting processing. The display screen 601 displays the target bone images 441 and 442 overlaid on the captured image, which are generated in advance based on the positions, sizes, and directions of the markers 221 and 222 and stored in the storage. For bone cutting support, the display screen 601 also displays the bone cutting plane image 431 selected in advance and stored in the storage such that the bone cutting plane image is overlaid on the surgery target bone image at the bone cutting position at the bone cutting angle.

A display screen 602 is a screen in which the bone cutting plane image 431 is made to match the depth direction of the display screen 602 by moving the patient's forearm or the camera position. When a bone cutting instrument 628 is placed on the bone along the bone cutting plane image 431 displayed on the display screen 602, and the bone is cut, very accurate bone cutting can be implemented.

<<Functional Arrangement of Information Processing Apparatus in Preoperative Preparation Data Generation System>>

Figure 7:
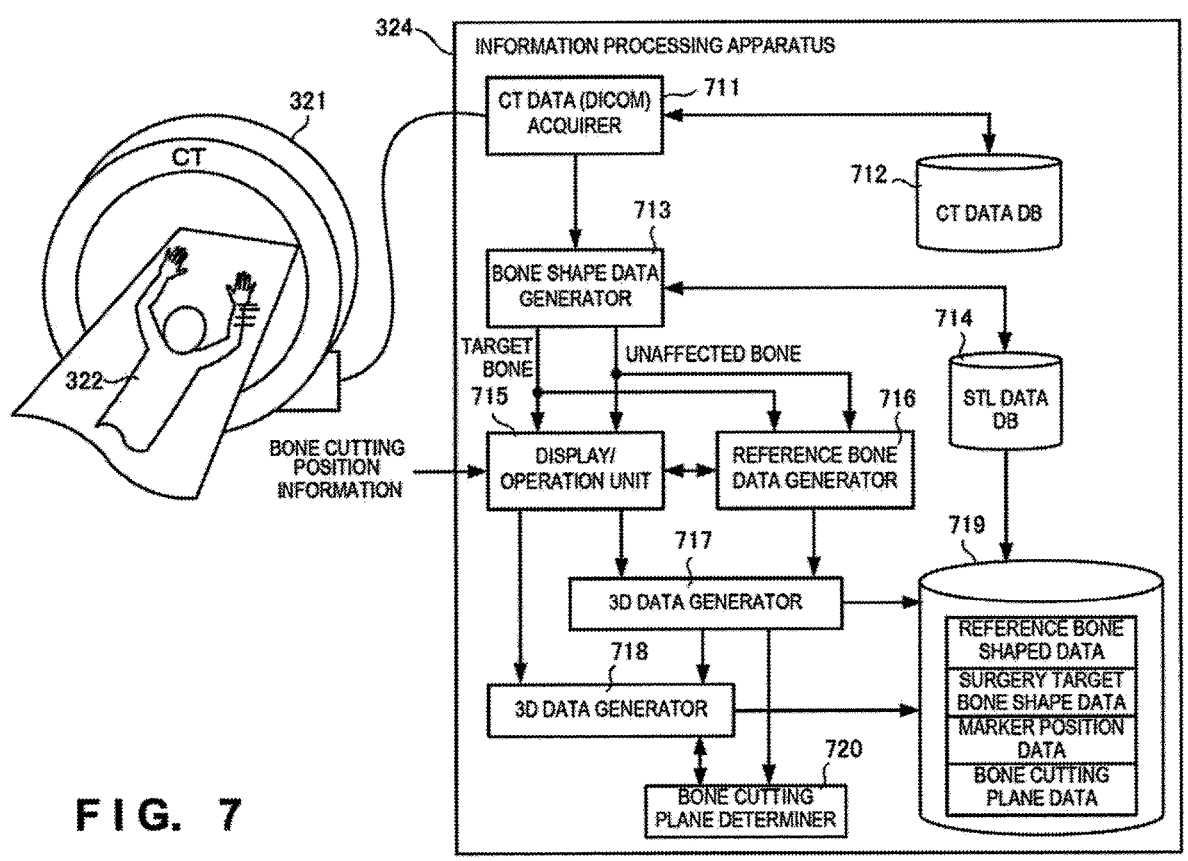
FIG. 7 is a block diagram showing the functional arrangement of an information processing apparatus according to the second embodiment of the present invention.

FIG. 7 is a block diagram showing the functional arrangement of the information processing apparatus 324. Note that FIG. 7 shows CT data as tomographic image data, and STL data as 3D bone surface model data. However, the data are not limited to these. Each functional unit of the information processing apparatus 324 is implemented when a CPU processes image data by executing a program using a memory.

A CT data acquirer 711 acquires CT data (DICOM) from the CT scanner 321 as an image of the patient 322. A CT database 712 searchably accumulates the CT data acquired by the CT data acquirer 711.

A bone shape data generator 713 generates STL data from the CT data as 3D bone surface model data. An STL data DB 714 searchably accumulates the STL data generated by the bone shape data generator 713.

A display/operation unit 715 is formed from a display, a touch panel, or the like. The display/operation unit 715 functions as a bone image display that performs 3D display of a bone image based on the STL data generated by the bone shape data generator 713, and performs 3D movement (rotation and movement) of the bone image in accordance with an instruction of the doctor. In this example, the image of the surgery target bone and the image of the unaffected bone of the patient 322 are displayed simultaneously such that they can be overlaid. The display/operation unit 715 can also input bone cutting position information of the surgery target bone. The display/operation unit 715 can independently display 3D movement (rotation and movement) of a plurality of partial bones (first target bone/second target bone) obtained by cutting and separating the surgery target bone at the bone cutting position. A reference bone data generator 716 laterally inverts the 3D data of the unaffected bone, thereby generating reference bone data.

A 3D data generator 717 overlays the 3D shape data of the first target bone separated based on the bone cutting position information and that of the reference bone in a virtual 3D space to generate 3D standard bone data. The generated 3D standard bone data is stored in a preoperative preparation data DB 719. A 3D data generator 718 generates 3D shape data of the second target bone. The generated 3D shape data is stored in the preoperative preparation data DB 719. Overlay of the target bone and the reference bone may be done based on an operation of the doctor or automatically performed by the 3D data generators 717 and 718 based on the bone shape (in particular, the shape of a joint portion). The preoperative preparation data DB 719 accumulates the 3D data generated by the 3D data generators 717 and 718 such that the 3D data can be searched by STL data. The STL data accumulated in the preoperative preparation data DB 719 is used by the intraoperative image processing system 500.

(STL Data DB)

Figure 8:
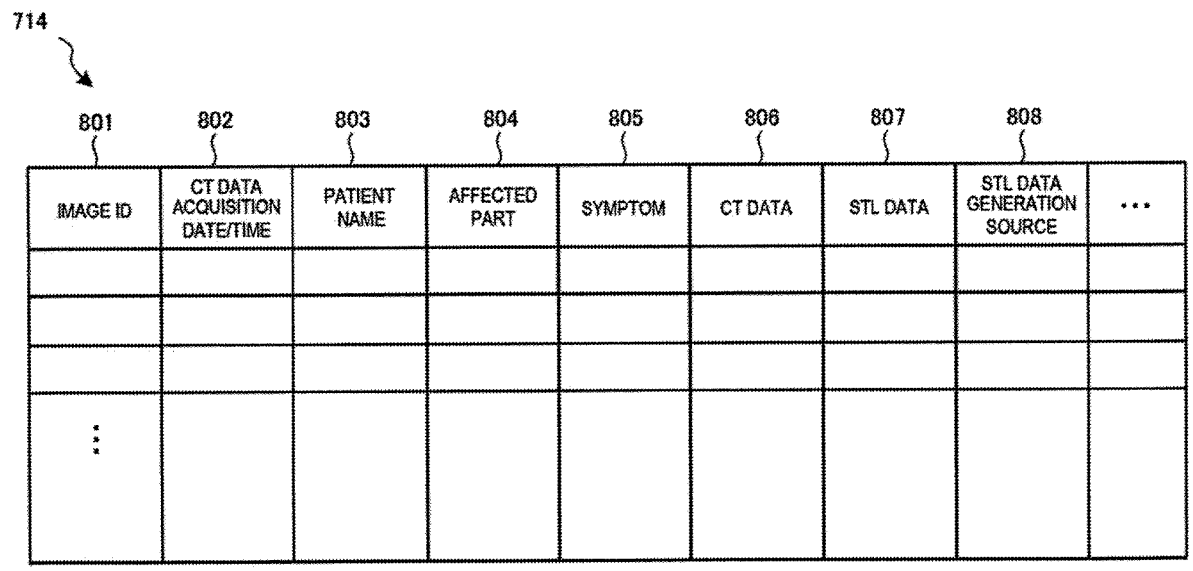
FIG. 8 is a view showing the arrangement of an STL data DB according to the second embodiment of the present invention.

FIG. 8 is a view showing the arrangement of the STL data DB 714 according to this embodiment. The STL data DB 714 searchably accumulates STL data representing a 3D bone surface model according to this embodiment.

The STL data DB 714 stores a CT data acquisition date/time 802, a patient name 803, an affected part 804, a symptom 805, and CT data 806 in association with an image ID 801. The STL data DB 714 also stores STL data 807 generated from the CT data 806, and an STL data generation source 808 if the STL data is externally generated.

(3D Preoperative Preparation Image DB)

Figure 9:
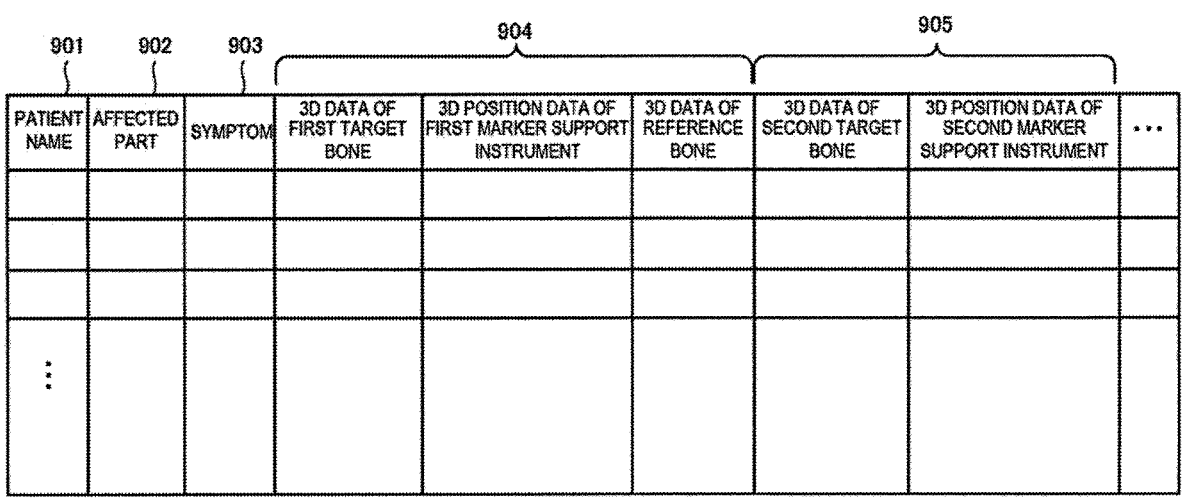
FIG. 9 is a view showing the arrangement of a preoperative preparation data DB according to the second embodiment of the present invention.

FIG. 9 is a view showing the arrangement of the preoperative preparation data DB 719 according to this embodiment. The preoperative preparation data DB 719 searchably accumulates STL data representing a 3D bone image according to this embodiment.

The preoperative preparation data DB 719 stores an affected part 902, a symptom 903, 3D data 904 associated with a first marker, and 3D data 905 associated with a second marker in association with a patient name 901. The 3D data 904 includes the 3D data of a first target bone, the 3D position data of a first marker support instrument, and the 3D data of a reference bone. The 3D data 905 includes the 3D data of a second target bone and the 3D position data of a second marker support instrument. Note that the 3D data 904 and 905 are stored in a format that allows a displayed bone image to move and rotate in the 3D space.

(Processing Procedure of Surgical Operation Support System)

Figure 10A:
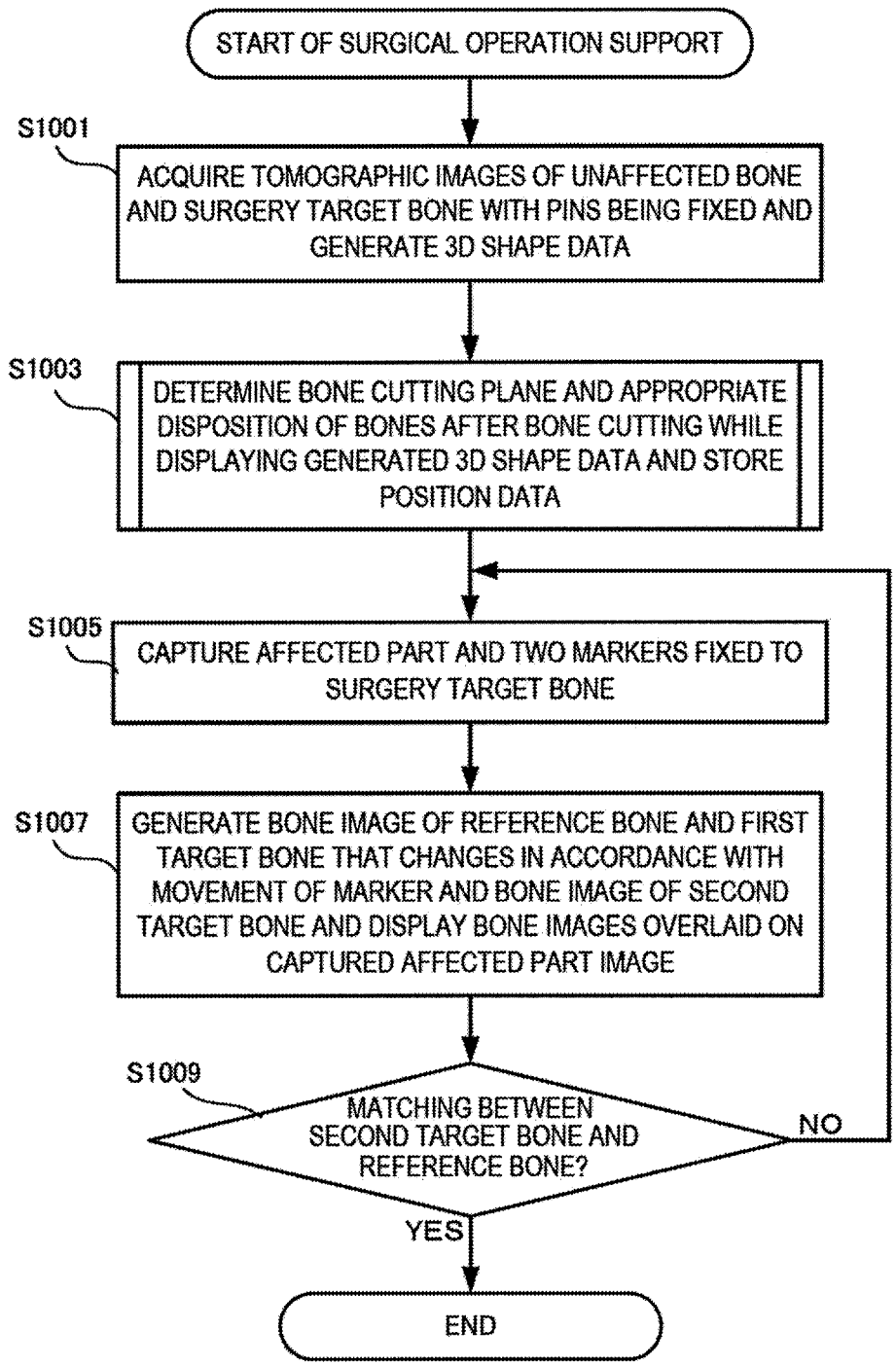
FIG. 10A is a flowchart showing the processing procedure of an entire surgical operation support system including a preoperative preparation data generation system and an intraoperative image processing system according to the second embodiment of the present invention.

FIG. 10A is a flowchart showing the processing procedure of the entire surgical operation support system including the preoperative preparation data generation system 320 and the intraoperative image processing system 500.

First, in step S1001, the preoperative preparation data generation system 320 acquires a tomographic image (for example, a CT image) of a surgery target bone to which pins are fixed and a tomographic image of an unaffected bone, and generates 3D data of the bones.

Next, in step S1003, while displaying the generated 3D shape data, the bone cutting plane image 431 and an appropriate disposition of the bone after bone cutting are determined, and the position data thereof are stored. Then, in step S1005, the intraoperative image processing system 500 captures markers fixed to the surgery target bone.

In step S1007, the intraoperative image processing system 500 generates a bone cutting plane image that changes in accordance with the movement of the marker, and displays the bone cutting plane image overlaid on the captured affected part image. The doctor places a blade on the bone in accordance with the bone cutting plane image while viewing the display screen and cuts the bone. The intraoperative image processing system 500 also generates and displays the bone images of the first target bone and the reference bone and the bone image of the second target bone. The doctor moves the forearm while viewing the display screen.

In step S1009, the intraoperative image processing system 500 confirms that the two target bones of the forearm are disposed such that the bone image of the second target bone matches the bone image of the reference bone. If the bone images do not match, the intraoperative image processing system 500 returns to step S1005 to continue the processing until the target bones are disposed at the matching position.

(Target Bone Image Separation Generation Processing)

Figure 10B:
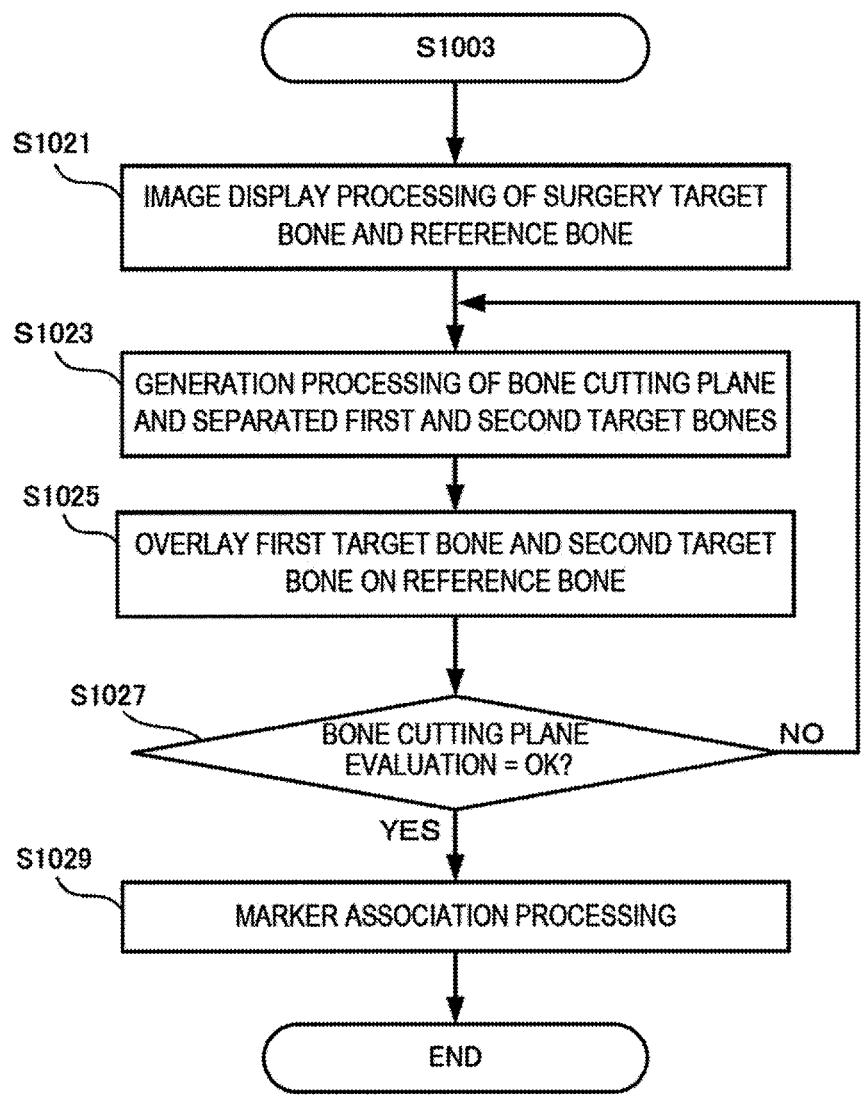
FIG. 10B is a flowchart showing the procedure of bone cutting plane generation processing shown in FIG. 10A according to the second embodiment of the present invention.

FIG. 10B is a flowchart showing the procedure of bone cutting plane generation processing (step S1003) shown in FIG. 10A.

In step S1021, the information processing apparatus 324 reads out the 3D shape data of the surgery target bone and the reference bone from the preoperative preparation data DB 719, and performs image display processing. In step S1023, a bone cutting plane is temporarily determined, and the 3D shape data of first and second target bones separated at the bone cutting plane are generated. The bone cutting plane may temporarily be determined based on a position designation by the doctor, or may be set at an appropriate position (for example, a position apart from an end by 3 cm) determined by the system. A bone cutting plane moving instruction input by the doctor using a pointing device or the like may be waited here. Upon receiving the moving instruction input, the information processing apparatus 324 moves the 3D data of the bone cutting plane in the 3D space in correspondence with the moving operation, and displays the 2D-converted bone cutting plane image.

In step S1023, the information processing apparatus 324 separates the target bone by the 3D data of the bone cutting plane, and generates the shape data of the separated bones (first and second target bones). The data of the set of the separated bone data and the bone cutting plane data is stored. In step S1025, the end of the first target bone of the two divided parts opposite to the bone cutting plane and the end of the second target bone opposite to the bone cutting plane are overlaid on the two ends of the reference bone. At this time, not only the positions but also the angles and directions are made to match those of the reference bone. In step S1027, the bone cutting plane is evaluated in that state. Various methods are usable to evaluate the bone cutting plane. For example, one of the following methods or a combination of a plurality of methods can be selected.

(1) Evaluation is done by visual recognition of the doctor (2) The feature points of the two ends are overlaid, and evaluation is done based on the non-overlay volume between the reference bone and the target bone (the smaller the non-overlay volume is, the higher the evaluation value is).

(3) The feature points of the two ends are overlaid, and evaluation is done based on the average of the vertical distances between the surfaces (the smaller the average is, the higher the evaluation value is).

(4) The feature points of the two ends are overlaid, and evaluation is done based on the volume of the target bone outside the reference bone (the smaller the volume is, the higher the evaluation value is).

(5) The feature points of the two ends are overlaid, and evaluation is done based on the overlay volume between the reference bone and the gap (absent part) between the target bones (the smaller the overlay volume is, the higher the evaluation value is).

If evaluation that meets a predetermined threshold is obtained in step S1027, the process advances to step S1029. If such evaluation is not obtained, the process returns to step S1021 to set the position and tilt of the bone cutting plane again. Until the evaluation value meets the predetermined threshold, the processing is repeated while sequentially changing the bone cutting plane, and an appropriate bone cutting plane is found. For example, as described above, at least the position and angle of an optimum bone cutting plane can be obtained by repeating a simulation using a plane of every direction as a bone cutting plane candidate while shifting the bone cutting position by a unit distance (for example, 1 mm) in the axial direction upward from the lowermost point of the surgery target bone 421. On, for example, a radius, a simulation is repeated using planes (for example, 300×24×72=about 500,000 planes) within the range of 60° to −60° with respect to a plane perpendicular to the bone axis in steps of 5°×5° as bone cutting plane candidates. The bone cutting plane may be changed downward from the uppermost point of the surgery target bone 421, as a matter of course. Alternatively, an optimum bone cutting plane may be found within a range set by the doctor.

In step S1029, the determined bone cutting plane and marker attachment information (the position, angle and size determined in advance to attach a marker and the marker type) are registered in the preoperative preparation data DB 719 in association with each other.

<<Functional Arrangement of Information Processing Apparatus in Intraoperative Image Processing System>>

FIG. 11 is a block diagram showing the functional arrangement of the tablet computer 501 in the intraoperative image processing system 500 according to this embodiment. Each functional unit of the tablet computer 501 is implemented when a CPU (not shown) executes a program using a memory. Note that in this embodiment, the tablet computer 501 is used. However, the present invention is not limited to this, and any information processing terminal including a display and a camera is usable. The camera or display/operation unit may be separated from the information processing apparatus, and data communication may be performed between them.

The camera 512 captures an affected part of the patient 322 in an operating room. The image capturing range of the camera 512 includes the markers 221 and 222 fixed at two points of the surgery target bone of the forearm 213 of the patient 322. A marker analyzer 1111 refers to a marker DB 1112, and analyzes the type of an image to be displayed and the position and direction to display the image from a marker image captured by the camera 512.

Preoperative preparation data 1119 is the same as the data stored in the preoperative preparation data DB 719 shown in FIG. 7. For example, the preoperative preparation data 1119 may be duplicated from the information processing apparatus 324 shown in FIG. 7 to the tablet computer 501 by communication or copied via a storage medium. Alternatively, the preoperative preparation data 1119 may be acquired by accessing from the tablet computer 501 to the preoperative preparation data DB 719 in the information processing apparatus 324 directly by communication.

A CG image generator 1114 generates a CG image to be displayed, based on the 3D position and direction of each marker acquired from the marker analyzer 1111, the 3D data of the target bone and the reference bone included in the preoperative preparation data 1119, and the like. The CG image generator 1114 functions as a first bone image generator that generates the bone image of the first target bone and the bone image of the reference bone from the 3D data of the first target bone and the 3D data of the reference bone based on the position, size, and direction of the captured first marker. The CG image generator 1114 also functions as a second bone image generator that generates the bone image of the second target bone from the 3D data of the second target bone based on the position, size, and direction of the captured second marker.

A display image generator 1115 overlays the surgery target bone image and the reference bone image generated by the CG image generator 1114 on the affected part image of the forearm 213 of the patient 322 captured by the camera 512 to generate display image data for the display. Using the image data, the display 511 simultaneously displays the target bone image and the reference bone image overlaid on the affected part image. It is also possible to display an image from a moved observation point or simultaneously display images from a plurality of observation points. That is, to search for the positions of the first marker and the second marker at which the second target bone overlaps the reference bone, the display image generator 1115 displays the bone image of the first target bone, the bone image of the reference bone, and the bone image of the second target bone. In this display, the display image generator 1115 displays the bone image of the first target bone and the bone image of the second target bone such that their relative positions change in accordance with a change in the relative positions of the first marker and the second marker.

(Marker DB)

Figure 12:
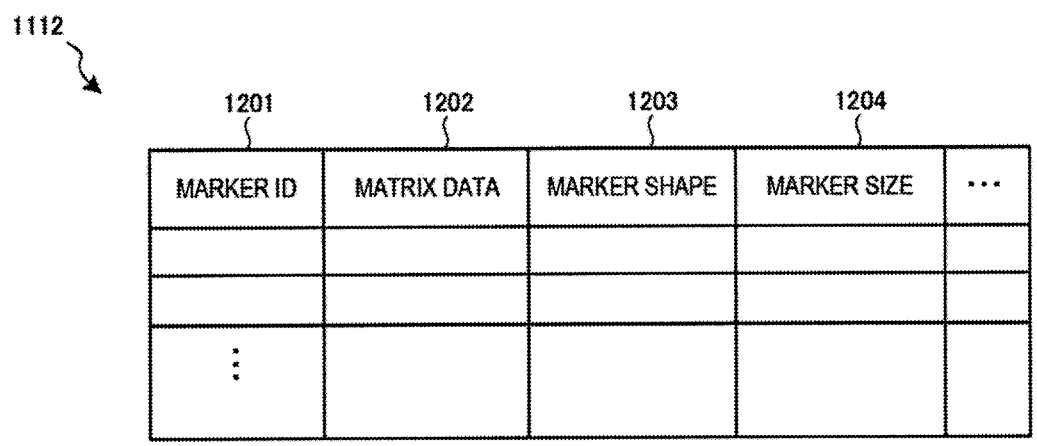
FIG. 12 is a view showing the arrangement of a marker DB according to the second embodiment of the present invention.

FIG. 12 is a view showing the arrangement of the marker DB 1112 according to this embodiment. The marker DB 1112 is used by the marker analyzer 1111 to analyze the 3D position and direction of each marker (that is, the position and direction of a pair of pins) from image data captured by the camera 512.

The marker DB 1112 stores matrix data 1202 of a 2D code in association with a marker ID 1201. Here, the matrix data 1202 arranges, for example, binary or multilevel bit data representing white/black or colors on 2D coordinates. A 3D position and direction can be recognized based on a change in coordinate values. Note that the 2D code is not limited to this. The marker DB 1112 also stores a marker shape 1203 and a marker size 1204.

(Marker Analysis Table)

Figure 13:
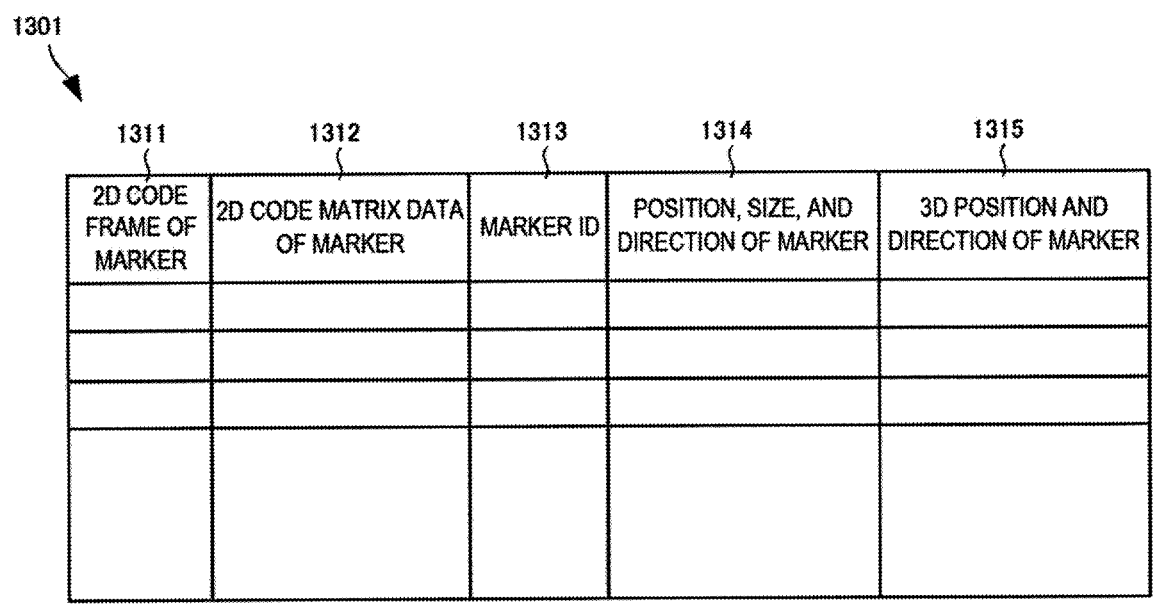
FIG. 13 is a view showing the arrangement of a marker analysis table used by a marker analyzer according to the second embodiment of the present invention.

FIG. 13 is a view showing the arrangement of a marker analysis table 1301 used by the marker analyzer 1111. The marker analysis table 1301 is a table used to obtain 2D data on the marker, the position, size, and direction of the marker, or 3D data of a marker support instrument from the image of a marker captured by the camera 512 and generate 3D display data of the target bone image or reference bone image.

The marker analysis table 1301 stores a 2D code frame 1311 of a marker extracted from a capture image, matrix data 1312 of the 2D code of the marker, and a marker ID 1313 discriminated from the matrix data 1312. The marker analysis table 1301 also stores a position, size, and direction 1314 of the marker, and a 3D position and direction 1315 of the marker calculated from the position, size, and direction 1314 of the marker. The position, size, and direction to display 3D data of the target bone to be displayed on the display can be determined in accordance with the 3D position and direction 1315 of the marker.

(3D Data Generation Table)

FIGS. 14 and 15 are views showing the arrangements of intraoperative image generation tables 1401 and 1501 used by the CG image generator 1114. The intraoperative image generation table 1401 stores analyzed 3D position data 1412 of the first marker, and 3D position data 1413 of the first marker stored in the preoperative preparation data DB 719 in association with a first target bone and reference bone ID 1411. Using a conversion vector that converts the 3D position data 1413 of the first marker into the 3D position data 1412, the coordinates of 3D data of the first target bone stored in the preoperative preparation data DB 719 are converted. The intraoperative image generation table 1401 stores 3D data 1414 of the first target bone for display, which is generated by the coordinate conversion. In addition, the coordinates of the 3D data of the reference bone stored in the preoperative preparation data DB 719 are converted using the same conversion vector, thereby generating and storing 3D data 1415 of the reference bone for display. The intraoperative image generation table 1401 also stores 3D data 1416 representing the position, shape, and tilt of the bone cutting plane in association with the first target bone and reference bone ID 1411.

The intraoperative image generation table 1501 stores analyzed 3D position data 1512 of the second marker, and 3D position data 1513 of the second marker stored in the preoperative preparation data DB 719 in association with a second target bone ID 1511. Using a conversion vector that converts the 3D position data 1513 of the second marker into the 3D position data 1512, the coordinates of 3D data of the second target bone stored in the preoperative preparation data DB 719 are converted. The intraoperative image generation table 1501 stores 3D data 1514 of the second target bone for display, which is generated by the coordinate conversion.

<<Processing Procedure of Information Processing Apparatus in Intraoperative Image Processing System>>

Figure 16:
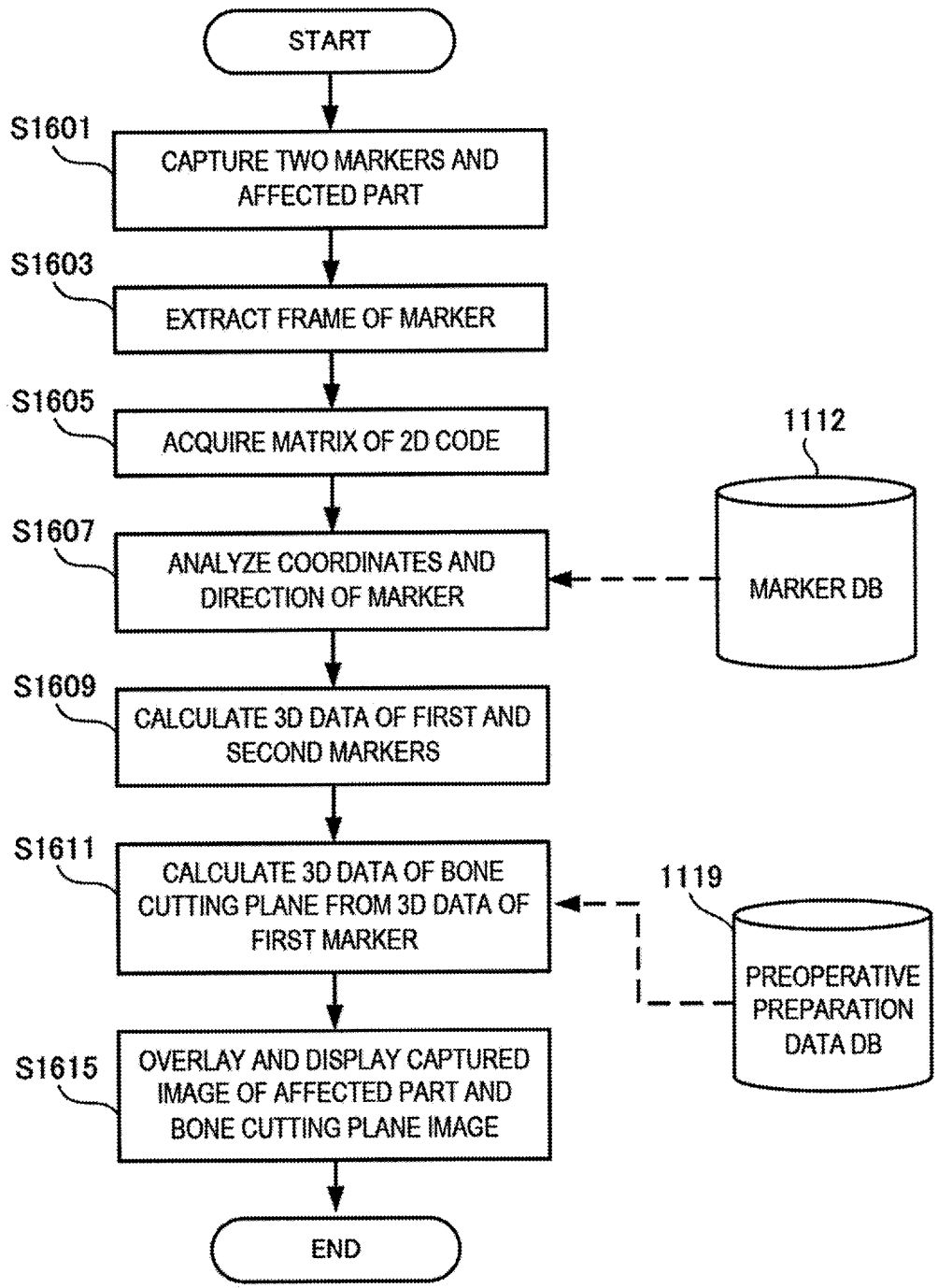
FIG. 16 is a flowchart showing the processing procedure of the tablet computer according to the second embodiment of the present invention.

FIG. 16 is a flowchart showing the processing procedure of the tablet computer 501 according to this embodiment. This flowchart is executed by the CPU of the tablet computer 501 using a RAM as an intraoperative image generation program to implement the functional components shown in FIG. 11.

In step S1601, the tablet computer 501 captures an affected area (in this example, the forearm portion) and acquires image data of two markers and the affected part image. In step S1603, the tablet computer 501 extracts a frame including a 2D code from the image data of the affected area. Note that in this example, the frame including the 2D code has a rectangular shape. However, a circular shape or any other shape is also usable. In step S1605, the tablet computer 501 acquires the matrix of the 2D code in the frame.

In step S1607, the tablet computer 501 compares the acquired matrix of the 2D code and the 2D code viewed from the front side, which is stored in the marker DB 1112, thereby specifying the marker. The tablet computer 501 also analyzes the marker coordinate system (the position and direction in the 3D space) in consideration of the position, size, and direction of the marker. In step S1609, the tablet computer 501 calculates the 3D data of the first marker fixed to the first target bone and the 3D data of the second marker fixed to the second target bone based on the analyzed positions and directions of the markers. In step S1611, the tablet computer 501 calculates the 3D data of the bone cutting plane based on 3D data stored as the preoperative preparation data 1119. In step S1615, the tablet computer 501 overlays and displays the captured affected part image and the generated bone cutting plane image.

According to this embodiment, since an appropriate disposition of the bone cutting plane can be determined and presented, accurate surgery is possible. It is possible to support an accurate disposition of the surgery target bone, accurate setting of the bone cutting position, creation of a necessary connecting bone, and proper bone setting processing at the time of surgery.

Third Embodiment

An information processing apparatus according to the third embodiment of the present invention will be described next. The information processing apparatus according to this embodiment is different from the second embodiment in that the shape of an absent part is generated, and the data of the absent part is accumulated. The rest of the components and operations is the same as in the second embodiment. Hence, the same reference numerals denote the same components and operations, and a detailed description thereof will be omitted. According to this embodiment, it is possible to generate an accurate implant based on the 3D data of an absent part.

FIG. 17 is a block diagram showing the functional arrangement of an information processing apparatus 1700 according to this embodiment. As shown in FIG. 17, an absent part shape generator 1721 is provided like a bone cutting plane determiner 720, and exchanges data with a 3D data generator 718. The absent part shape generator 1721 generates 3D shape data (a gap 443 in an image 404 shown in FIG. 4) from the shape of a gap in a case in which surgery target bones (first and second target bones) separated into two parts at the bone cutting plane determined by the bone cutting plane determiner 720 are overlaid on the two ends of a reference bone. The 3D shape data of the gap is stored in a preoperative preparation data DB 719 as absent part shape data.

Figure 18:
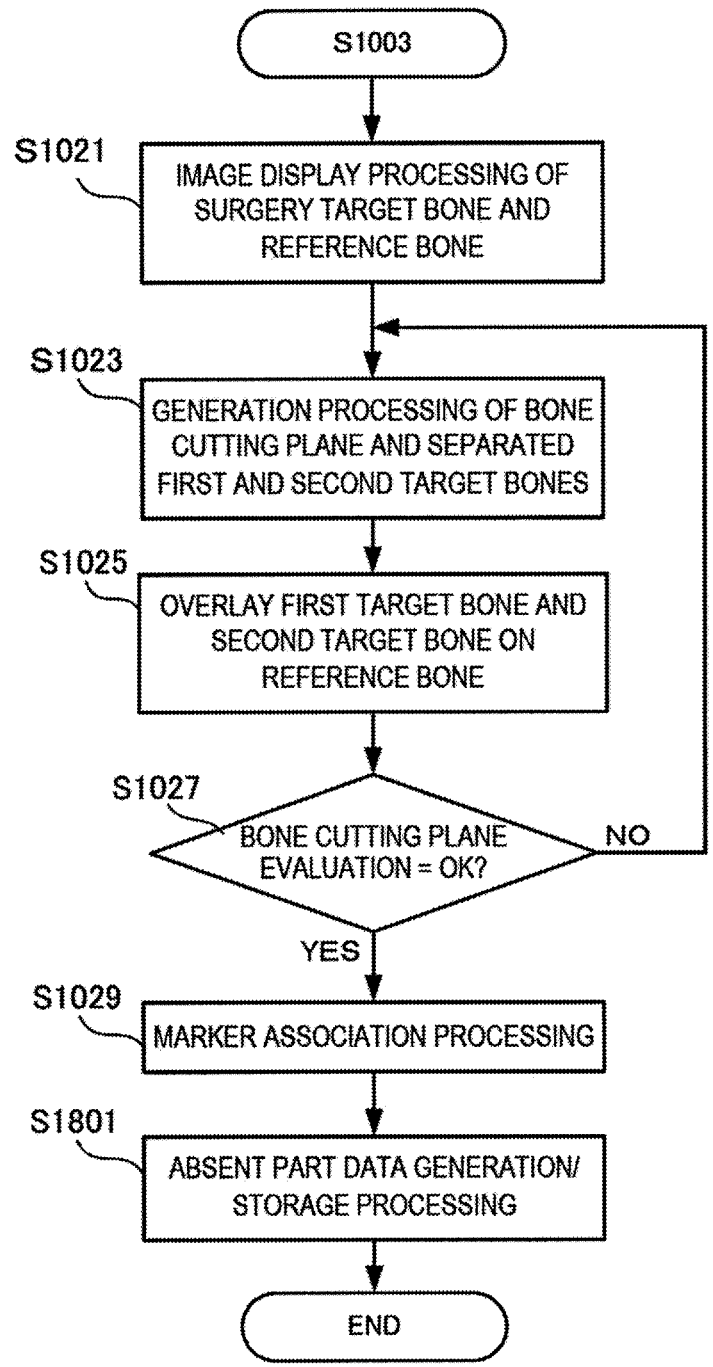
FIG. 18 is a flowchart showing the procedure of bone cutting plane generation processing according to the third embodiment of the present invention.

FIG. 18 is a flowchart showing the procedure of bone cutting plane generation processing (step S1003) according to this embodiment. In step S1801, the shape data of an absent part is generated as described above using the data of a determined bone cutting plane, and stored in the preoperative preparation data DB 719.

According to this embodiment, it is possible to generate an accurate implant using the shape data of an absent part.

Fourth Embodiment

An information processing apparatus according to the fourth embodiment of the present invention will be described next. The information processing apparatus according to this embodiment is different from the second embodiment in that a bone cutting position candidate is selected and notified. The rest of the components and operations is the same as in the second embodiment or the third embodiment. Hence, the same reference numerals denote the same components and operations, and a detailed description thereof will be omitted.

<<Functional Arrangement of Information Processing Apparatus>>

FIG. 19 is a block diagram showing the functional arrangement of an information processing apparatus 1900 according to this embodiment. Note that the same reference numerals as in FIG. 7 denote the same functional components in FIG. 19, and a description thereof will be omitted.

Referring to FIG. 19, a bone cutting position candidate selector 1921 is added. The bone cutting position candidate selector 1921 displays at least one appropriate bone cutting plane and presents it to a doctor as a bone cutting position candidate.

Note that determination and evaluation of the appropriate bone cutting plane are done based on the degree of overlay in a case in which target bones separated by a bone cutting plane determiner 720 are overlaid on a reference bone image or the size or shape of an absent part, as described above. As for the degree of overlay, when the cumulative value of errors or the maximum value of errors is small, or the number of errors equal to or more than a predetermined threshold is small, the degree of matching is determined to be high. In addition, a weight may be added to an error in an important part of a bone, for example, a joint portion.

In addition to the above-described example, considering that the range of the bone cutting position is limited based on the symptom of the surgery target bone, the doctor may manually input the range in advance. The bone cutting position candidate selector 1921 may automatically limit the range based on the information of the surgery target bone or symptom and then start selecting a bone cutting position candidate.

The doctor may confirm a bone cutting position candidate selected by the bone cutting position candidate selector 1921 again and adjust the position. Alternatively, when a plurality of bone cutting position candidates are selected, the overlay state may be displayed while automatically switching the bone cutting position candidate, and the bone cutting position may be determined based on observation of the doctor.

<<Processing Procedure of Information Processing Apparatus>>

Figure 20:
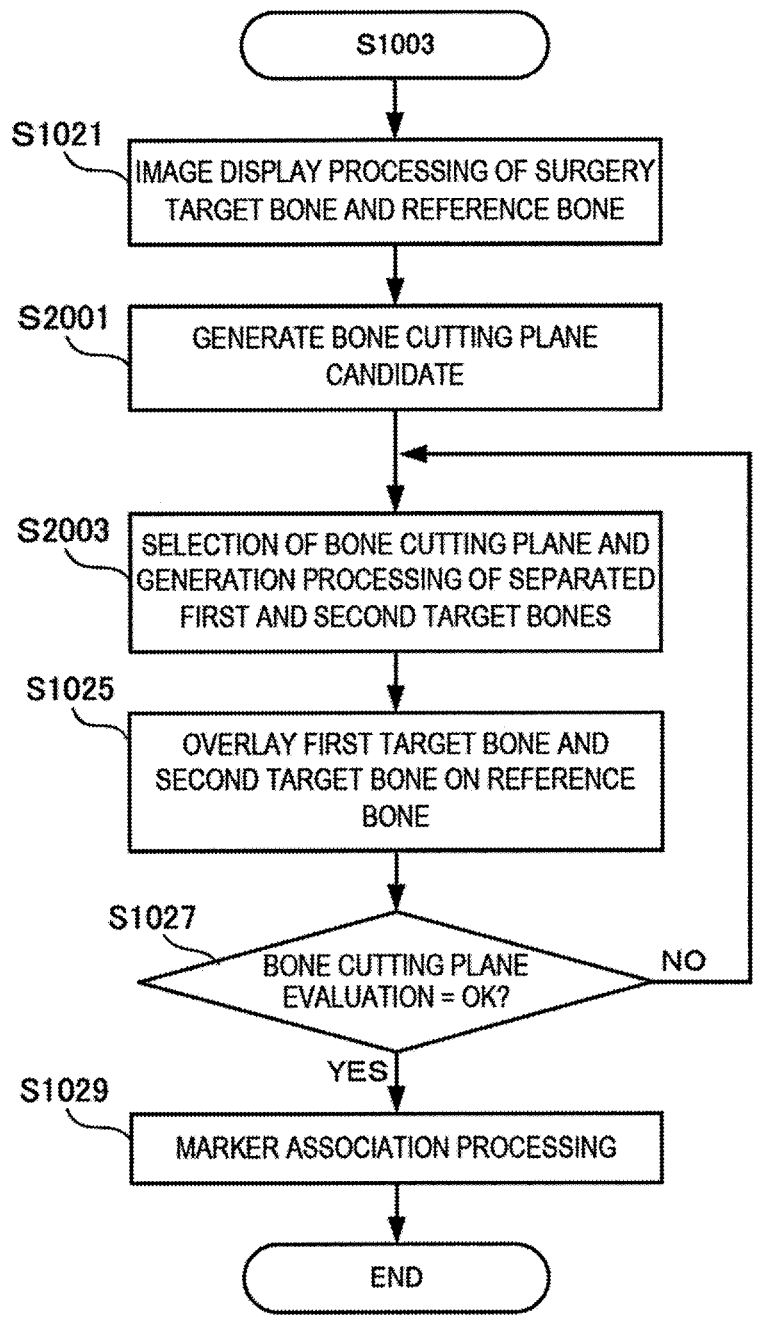
FIG. 20 is a flowchart showing the processing procedure of the information processing apparatus according to the fourth embodiment of the present invention.

FIG. 20 is a flowchart showing the processing procedure of the information processing apparatus 1900 according to this embodiment. Note that the same step numbers as in FIG. 8 denote the same steps in FIG. 20, and a description thereof will be omitted.

In step S2001, the information processing apparatus 1900 performs a bone cutting simulation within a bone cutting range corresponding to a surgery target bone or its symptom, thereby generating a bone cutting plane candidate that meets an optimum condition (for example, minimization of an absent part size). Not only one but a plurality of bone cutting plane candidates may be generated. In step S2003, the doctor selects one bone cutting plane from the selected bone cutting plane candidates.

According to this embodiment, it is possible to more easily and accurately determine a bone cutting plane.

Fifth Embodiment

A bone cutting support system according to the fifth embodiment of the present invention will be described next. The bone cutting support system according to this embodiment is different from the second to fourth embodiments in that when generating preoperative preparation data, virtual 3D markers are generated on a screen and created by a 3D printer without disposing actual markers on a target bone. The rest of the components and operations is the same as in the above-described embodiments. Hence, the same reference numerals denote the same components and operations, and a detailed description thereof will be omitted.

<<Outline of Bone Cutting Support System>>

The outline of processing of the bone cutting support system according to this embodiment will be described with reference to FIGS. 21A and 21B.

(Preoperative Preparation Data Generation Processing)

FIG. 21A is a view for explaining the outline of preoperative preparation image generation processing using the information processing apparatus according to this embodiment. Note that the same reference numerals as in FIG. 4 denote the same display images or display elements in FIG. 21A. Note that the images are CG images displayed on the display screen, which correspond to the stages of the preoperative preparation data generation processing, respectively.

In the second stage, as indicated by an image 2102, the surgery target bone of a forearm 213 is internally captured by CT scan or the like, and thus generated 3D data (to be referred to as a surgery target bone hereinafter) 421 of the surgery target bone (affected bone) is displayed. The surgery target bone 421 is generated from captured STL data, and 3D markers 2111 and 2112 planned and drawn on the 3D data are virtually displayed (indicated by broken lines in FIG. 21A). A reference bone image 412 and the surgery target bone 421 are compared on the display screen, and the state of the surgery target bone 421 is confirmed.

In the third stage, the surgery target bone 421 is manipulated on an image 403 while referring to an enlarged display image 2105 in which the observation point in the 3D space is moved close to the surgery target bone or a divided display image 406 in which a plurality of images from different observation points (in this example, images from three directions) are simultaneously displayed. That is, the surgery target bone 421 is moved and rotated with respect to the reference bone image 412 to overlay the end portions of the reference bone image 412 on the end portions of the surgery target bone 421.

If the bone cutting plane can be estimated to exist on the upper end side, first, the lower ends of the surgery target bone 421 and the reference bone image 412 are overlaid to determine the bone cutting plane of the surgery target bone 421, as shown on the left side. In particular, the shapes (feature points) of the joint portions (the lower ends or upper ends in the drawing) are overlaid to recognize the distortion, bending, or deformation of the surgery target bone 421. Then, the bone is compared with the reference bone gradually upward from the lower end, and a branch position where deviation from the reference bone starts is determined as a bone cutting plane image 431. Here, the bone cutting plane image 431 is a rectangular plane having a predetermined shape and size. However, the present invention is not limited to this. A plane including a curved plane may be used in accordance with the purpose of bone cutting.

Note that the doctor may evaluate and determine the bone cutting plane image 431 while observing the overlay state between the reference bone image 412 and the surgery target bone 421. However, an optimum bone cutting plane may be obtained by calculation. For example, the lower ends are overlaid, and a non-overlay volume per unit length in the axial direction between the surgery target bone 421 and the reference bone image 412 is calculated sequentially from the lower end. Uppermost points at which the non-overlay volume does not exceed a predetermined value may be connected to form a plane serving as the bone cutting plane image 431. Alternatively, the surface of the reference bone image 412 may finely be divided into unit areas, and positions at which the distance in the vertical direction up to the surface of the surgery target bone 421 exceeds a predetermined value on a unit area basis may be connected to automatically derive the bone cutting plane image 431. Otherwise, when two target bone images 441 and 442 generated by bone cutting are overlaid on the upper and lower ends of the reference bone image 412, as indicated by an image 2104, the bone cutting plane may be determined such that the sum of volumes outside the reference bone image 412 (or the distances between the surfaces) is minimized. Alternatively, when the two target bone images 441 and 442 generated by bone cutting are overlaid on the upper and lower ends of the reference bone image 412, as indicated by the image 2104, the bone cutting plane may be determined such that a gap (absent part) 443 between the separated bones of the target bone images 441 and 442 is minimized. At any rate, the position and angle of an optimum bone cutting plane can be obtained by repeating a simulation using a plane of every direction as a bone cutting plane candidate while shifting the position by a unit distance (for example, 1 mm) in the axial direction of the surgery target bone 421. On, for example, a radius, for example, 300×24×72=about 500,000 planes are obtained as bone cutting plane candidates within the range of 60° to −60° with respect to a plane perpendicular to the bone axis in steps of 5°×5°.

When the bone cutting plane image 431 is thus determined, in the fourth stage, the 3D data of the two target bone images 441 and 442 obtained by separating the surgery target bone 421 by the bone cutting plane image 431 are generated and stored. That is, the set of the target bone image 442 and the reference bone image 412 which are overlaid is stored in association with the virtually drawn 3D marker 2112. As indicated by the image 2104, the target position of the target bone image 441 with respect to the target bone image 442 or the reference bone image 412 is stored in association with the position data of the virtually drawn 3D marker 2111. Note that the base blocks of the virtually drawn 3D markers 2111 and 2112 are designed such that the surface matches the characteristic part of the target bone. Hence, in the 3D markers produced by the 3D printer, if the shapes of the base blocks of the virtually drawn 3D markers 2111 and 2112 can be reproduced, the 3D markers produced by the 3D printer can accurately indicate the position and direction of the target bone. That is, if the position or tilt of the 3D marker produced by the 3D printer can be recognized in the real space, the target position or tilt of the target bone image 441 can be estimated.

Furthermore, the data of the position, shape, and tilt of the bone cutting plane image 431 are stored in association with the position data of the drawn 3D marker 2111 or 2112. The position and direction of a 2D marker bonded to the 3D marker 2111 and the position and direction of a 2D marker bonded to the 3D marker 2112 are determined in advance.

By using the thus prepared data, display of the target bone image 441 and the reference bone image 412, display of the target bone image 442, and display of the bone cutting plane image 431 can be performed based on the positions, sizes, and directions of the 3D markers placed on the target bone and captured in surgery. Note that the gap 443 between the target bone image 441 and the target bone image 442 represents the shape of a connecting bone necessary in surgery. Hence, the 3D shape of the connecting bone necessary in surgery can also be acquired at this time.

Note that in surgery, the combination of the target bone images 441 and 442 determined as the target disposition on the image 2104 may integrally be used and displayed without using the reference bone image 412 generated from the unaffected side. In this case, the positions of the 3D markers 2111 and 2112 in a state in which both of the target bone images 441 and 442 are overlaid on the reference bone image 412 are stored in the storage as target relative position data.

In this embodiment, since corrective osteotomy of an affected bone (surgery target bone) with malunion is carried out, target bones on both sides of the bone cutting plane are taken into consideration. However, the present invention is not limited to this. For example, in artificial joint transplant surgery, bone cutting planes (for example, three planes) used to generate planes to which an artificial joint is to be attached are displayed using the above-described AR technology, thereby implementing accurate bone cutting. For example, 3D CG models of artificial joints in three sizes S, M, and L are prepared. When healing osteoarthritis, the unaffected bone is CT-scanned, and each artificial joint model, is overlaid on the 3D data of the surgery target bone in a 3D virtual space. The relative positional relationship between a 3D marker and the bonding surface of the artificial joint model is stored, and a blade model is AR-displayed according to the bonding surface during surgery. A blade representing the bone cutting plane may be pasted to the 3D model of the artificial joint. In this case, one 3D marker suffices. Note that a 3D marker may be attached to an actual blade, the 3D marker position may be recognized, and movement of the blade to the target position may be instructed.

(Bone Cutting Support Processing During Surgery)

Figure 21B:
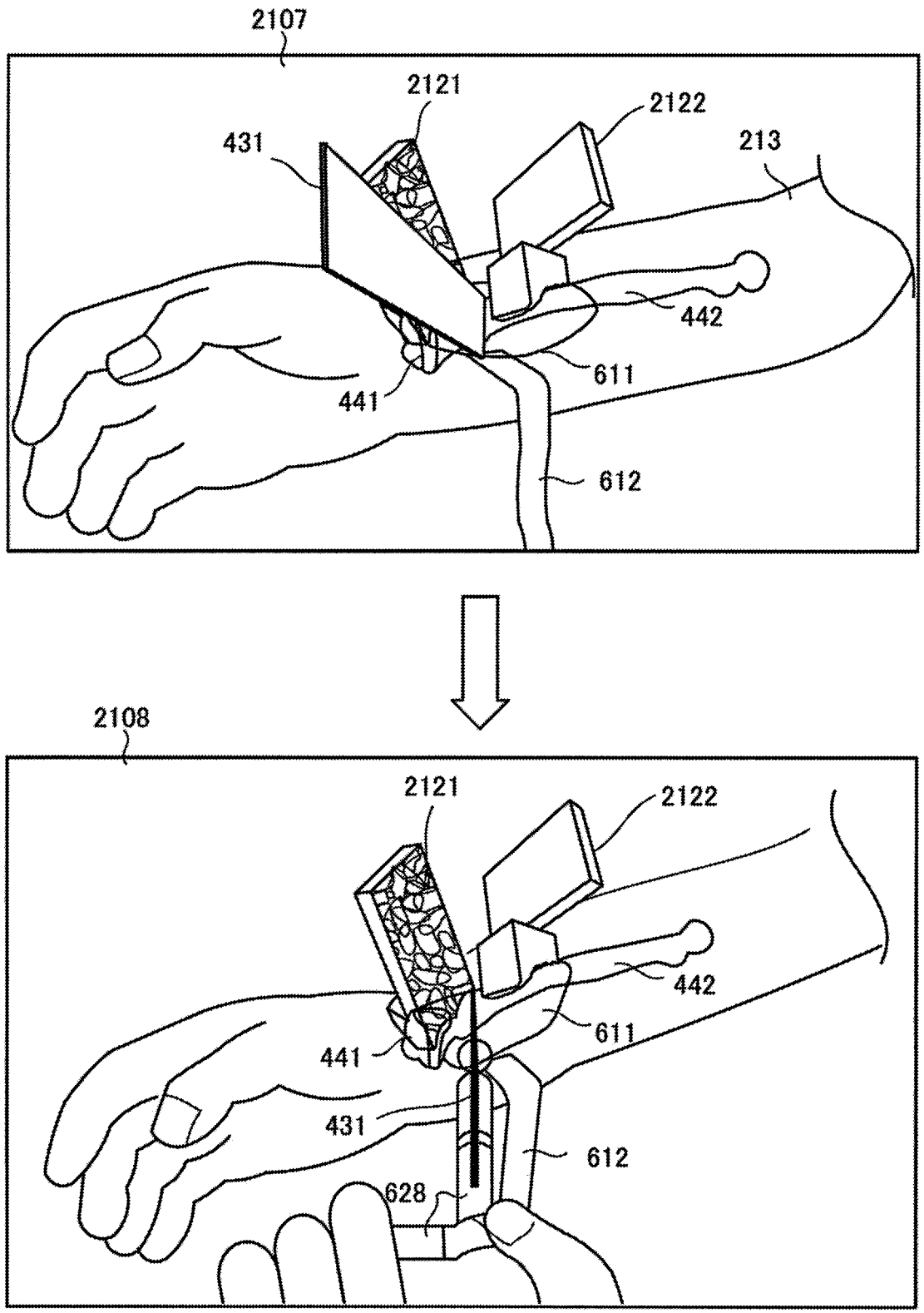
FIG. 21B is a view for explaining the outline of bone cutting support processing during surgery according to the fifth embodiment of the present invention.

FIG. 21B is a view for explaining the outline of bone cutting support processing during surgery according to this embodiment. Note that the same reference numerals as in FIG. 6B denote the same elements in FIG. 21B.

A display screen 2107 displays an affected part (the forearm portion of the left hand) 213 with a forearm radius as a surgery target bone in the living body, and 3D markers 2121 and 2122 whose base blocks are fixed to the surgery target bones, respectively, which are captured by the camera. The display screen 2107 also displays an incision part 611 for bone cutting, and a holding instrument 612 that holds the incision part 611 in an open state for bone cutting processing. The display screen 2107 displays the target bone images 441 and 442 overlaid on the visually recognized affected part, which are generated in advance based on the positions, sizes, and directions of the 3D markers 2121 and 2122 and stored in the storage. For bone cutting support, the display screen 2107 also displays the bone cutting plane image 431 selected in advance and stored in the storage such that the bone cutting plane image is overlaid on the surgery target bone image at the bone cutting position at the angle to cut the bone.

A display screen 2108 is a screen in which the bone cutting plane image 431 is made to match the depth direction of the display screen 2107 by moving the patient's forearm or the camera position. When a bone cutting instrument 628 is placed on the bone along the bone cutting plane image 431 displayed on the display screen 2108, and the bone is cut, very accurate bone cutting can be implemented.

<<Processing Procedure of Bone Cutting Support System>>

FIG. 22 is a flowchart showing the processing procedure of the entire bone cutting support system including a preoperative preparation data generation system and an intraoperative image processing system according to this embodiment.

In step S2201, the bone cutting support system performs CT imaging of the affected part of a patient. In step S2203, the bone cutting support system forms a 3D model based on, for example, STL data. In step S2205, the bone cutting support system makes preoperative planning while displaying the 3D data. For example, a 3D marker is generated on the screen, and data to produce the 3D marker is generated. In addition, the 3D marker is associated with a surgery target bone and a bone cutting plane, a bone hole, an implant, and the like necessary for procedures needed during surgery on 3D coordinates. In step S2207, the bone cutting support system produces a 3D marker having a base block matching the target bone by a 3D printer based on the data of the 3D marker.

In step S2209, the bone cutting support system inputs the processing program of an intraoperative application and each data associated with the 3D marker. In step S2211, the bone cutting support system executes bone cutting support based on the processing program of the intraoperative application and each data associated with the 3D marker.

<<Functional Arrangement of Preoperative Preparation Data Generation System>>

Figure 23:
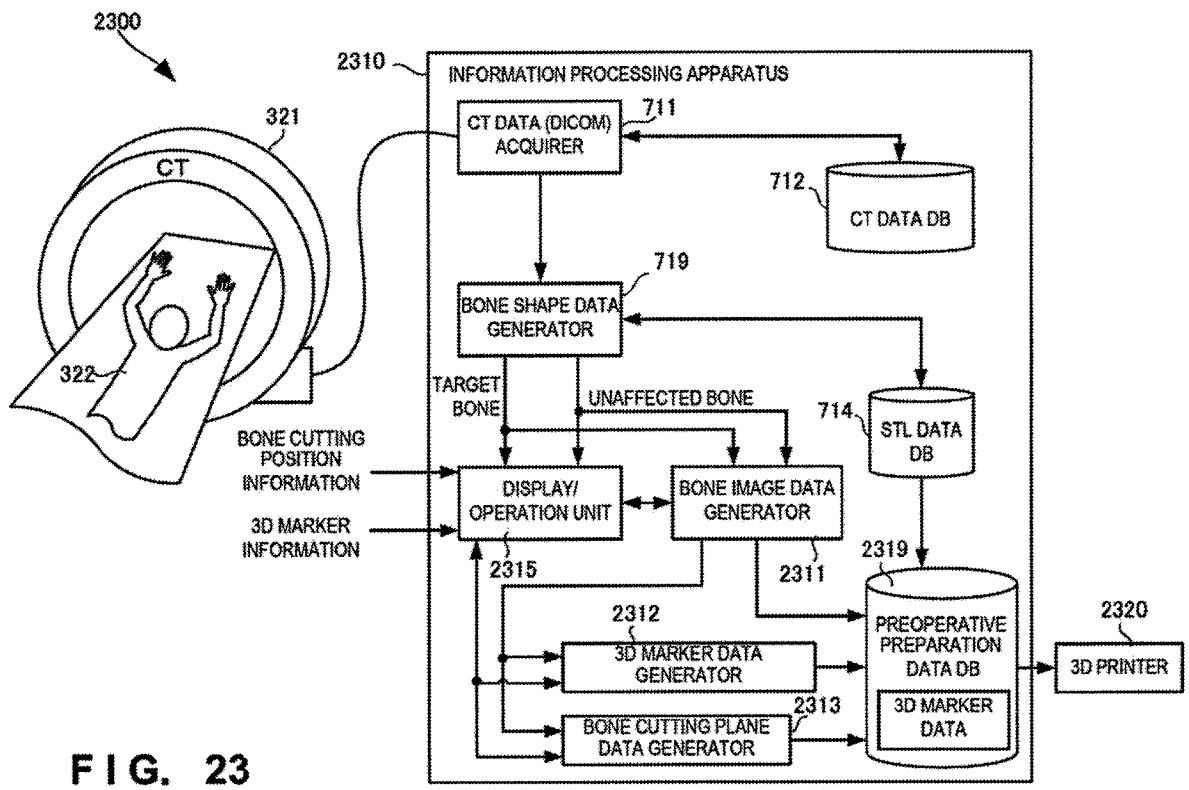
FIG. 23 is a block diagram showing the functional arrangement of the preoperative preparation data generation system according to the fifth embodiment of the present invention.

FIG. 23 is a block diagram showing the functional arrangement of a preoperative preparation data generation system 2300 according to this embodiment. Note that the same reference numerals as in FIG. 7 denote the same functional components in FIG. 23, and a description thereof will be omitted.

As shown in FIG. 23, when capturing an affected part by a CT 321, no marker is placed on a patient 322. A bone image data generator 2311 is a functional component including the reference bone data generator 716 and the 3D data generators 717 and 718 shown in FIG. 7. A 3D marker data generator 2312 generates 3D data of a 3D marker generated based on 3D marker information input to a display/operation unit 2315. A 3D marker data generator 2313 generates 3D data of a bone cutting plane generated based on bone cutting position information input to the display/operation unit 2315. Note that if a bone cutting plane prepared in advance is to be used, the data may be stored in an STL data DB 714 in advance. A preoperative preparation data DB 2319 stores 3D data of a 3D marker in addition to data on a preoperative preparation data DB 719 shown in FIG. 7, and stores 3D data of a surgery target bone, a bone cutting plane, and the like in association with the 3D data of the 3D marker.

A 3D printer 2320 produces a 3D marker based on 3D printer data generated from the 3D data of the 3D marker.

(Preoperative Preparation Data DB)

FIG. 24 is a view showing the arrangement of the preoperative preparation data DB 2319 according to this embodiment. FIG. 24 shows the arrangement of preparation data planned in a technique unique to this embodiment. Note that FIG. 24 also includes the arrangement illustrated in FIG. 9.

The preoperative preparation data DB 2319 stores an affected part 2402 and a technique 2403 in association with a patient name 2401. In this example, the affected part is the right arm, and the technique is malunion surgery of a distal radius. The preoperative preparation data DB 2319 also stores a planning item 2404 necessary for the affected part 2402 and the technique 2403, and 3D data necessary for the planning item in association with a 3D marker. In this example, the preoperative preparation data DB 2319 stores 3D data of a 3D marker produced by a 3D printer 2420 and 3D data of a bone cutting plane corresponding to it.

<<Procedure of Bone Cutting Plane Generation Processing>>

FIG. 25 is a flowchart showing the procedure of bone cutting plane generation processing according to this embodiment. This flowchart is executed by the CPU of the information processing apparatus 2310 using a RAM to implement the functional components shown in FIG. 23.

In step S2501, the information processing apparatus 2310 acquires a CT image of a target bone of the patient and, if necessary, a CT image of an unaffected bone. In step S2503, the information processing apparatus 2310 generates STL data from the CT image data. When requesting an external apparatus to generate STL data, the information processing apparatus 2310 acquires the STL data.

In step S2507, the information processing apparatus 2310 acquires bone cutting plane position information and 3D marker shape and placement position information. In step S2509, the information processing apparatus 2310 generates 3D data of the bone cutting plane, 3D marker data, and the like in association with the 3D data of the STL bone. In step S2511, the information processing apparatus 2310 associates the generated 3D data and stores them in the preoperative preparation data DB 2319. In step S2513, the information processing apparatus 2310 outputs the 3D marker data for the 3D printer.

<<Functional Arrangement of Intraoperative Image Processing System>>

Figure 26:
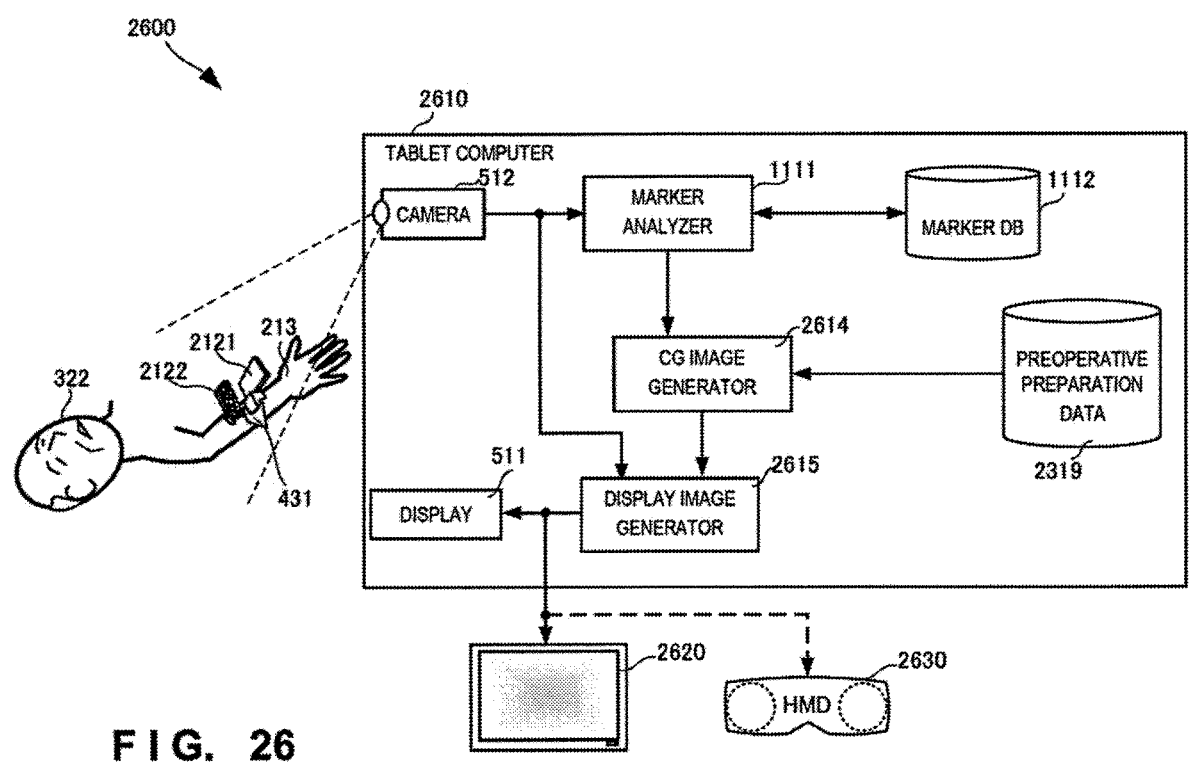
FIG. 26 is a block diagram showing the functional arrangement of a tablet computer in the intraoperative image processing system according to the fifth embodiment of the present invention.

FIG. 26 is a block diagram showing the functional arrangement of a tablet computer 2610 in an intraoperative image processing system 2600 according to this embodiment. The same reference numerals as in FIG. 3, 5, or 11 denote the same functional components in FIG. 26, and a description thereof will be omitted.

The preoperative preparation data DB 2319 stores the same preparation data generated by the preoperative preparation data generation system 2300 shown in FIG. 23. A CG image generator 2614 performs 3D coordinate conversion of 3D data of the surgery target bone, the bone cutting plane, and the like from the preoperative preparation data DB 2319 in correspondence with the position and direction of the 3D marker from a marker analyzer 1111, thereby generating a CG image to be overlaid on a visible surgery part. A display image generator 2615 converts the image generated by the CG image generator 2614 into a display image to be displayed on a display 511, an external monitor 2620, or an HMD 2630. Note that in this embodiment, an optical see-through HMD is preferably used.

Note that the processing procedure of the tablet computer 2610 in the intraoperative image processing system 2600 is similar to that shown in FIG. 16 except that a marker is created by the 3D printer 2320 as a 3D marker to be placed on each target bone in surgery, and an illustration and description thereof will be omitted.

According to this embodiment, during surgery, a 3D marker produced by the 3D printer is placed so as to match the shape of a bone during surgery. This makes it possible to support bone cutting without forming holes in the surgery target bone of the patient and placing markers before and during surgery.

Sixth Embodiment

A bone cutting support system according to the sixth embodiment of the present invention will be described next. The bone cutting support system according to this embodiment is different from the second to fifth embodiments in that 3D data of a target bone is acquired by a depth sensor in intraoperative image processing using, as a marker, 3D data of the surface of a part in which the surgical operation of a target bone is performed, thereby supporting bone cutting. The rest of the components and operations is the same as in the above embodiments. Hence, the same reference numerals denote the same components and operations, and a detailed description thereof will be omitted.

Note that preoperative preparation data according to this embodiment is similar to that of the above-described embodiments except that separate marker information is not included because the 3D surface image of the surgery target bone is used as a marker, and a description thereof will be omitted. In the following embodiment, a case in which an HMD and a depth sensor are integrated will be described. If the HMD and the depth sensor are separated, position determination needs to be done by adding a marker to a position sensor (for example, GPS) or depth sensor.

<<Functional Arrangement of Intraoperative Image Processing System>>

Figure 27:
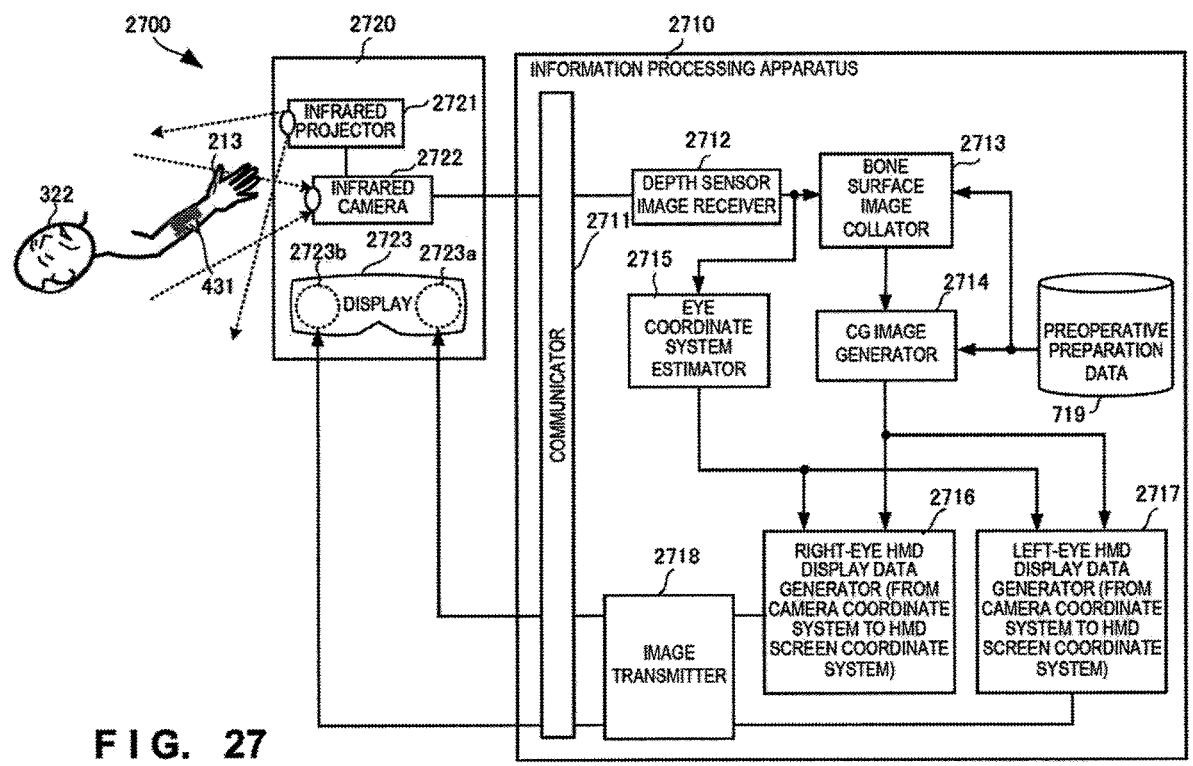
FIG. 27 is a block diagram showing the functional arrangement of an intraoperative image processing system according to the sixth embodiment of the present invention.

FIG. 27 is a block diagram showing the functional arrangement of an intraoperative image processing system 2700 according to this embodiment. The intraoperative image processing system 2700 includes a depth sensor & HMD 2720 and an information processing apparatus 2710.

A depth sensor & HMD 2720 includes a depth sensor and an optical see-through HMD. Note that the depth sensor and the HMD may be separate but are preferably integrated. The depth sensor is formed from an infrared projector 2721 and an infrared camera 2722, and acquires a depth image (distance image) of a surgery part during surgery. The distance image is equivalent to the 3D image of a surface. A 3D bone cutting plane 431 is displayed on a display 2723 (right-eye unit 2723*a*/left-eye unit 2723*b*) of the binocular HMD such that its 3D position is overlaid on the visible affected part of a patient 322.

A communicator 2711 of the information processing apparatus 2710 controls data transmission/reception to/from the depth sensor and the HMD of the depth sensor & HMD 2720. A depth sensor image receiver 2712 receives a depth image (distance image). A bone surface image collator 2713 performs collation with a characteristic surface image of a target bone image of preoperative preparation data 719 using the depth image (distance image) as a marker. A CG image generator 1714 performs 3D coordinate conversion of the 3D data of the preoperative preparation data 719 in correspondence with a change in the position and direction necessary for collation of the bone surface obtained from the bone surface image collator 2713, thereby generating a CG image. Note that the preoperative preparation data 719 according to this embodiment does not need a separate marker. Hence, in FIG. 7, the preoperative preparation data 719 includes no marker position data, or stores detailed 3D data of the characteristic surface shape of the surgery part of the surgery target bone as marker position data.

An eye coordinate system estimator 2715 estimates an eye coordinate system based on the line of sight or visual field of the doctor wearing the HMD from depth sensor image data. A right-eye HMD display data generator 2716 refers to eye coordinate system information from the eye coordinate system estimator 2715, and converts display image data on a 3D camera coordinate system into right-eye display data for a 2D HMD screen coordinate system. A left-eye HMD display data generator 2717 refers to the eye coordinate system information from the eye coordinate system estimator 2715, and converts display image data on the 3D camera coordinate system into left-eye display data for the 2D HMD screen coordinate system. The display position of the converted display data for the 2D HMD screen coordinate system is adjusted such that the 3D target bone image and the reference bone image overlap the forearm 213 of the affected part seen through the display 2723 of the HMD. It is also possible to display an image from a moved observation point or simultaneously display images from a plurality of observation points. Note that image display conversion by moving the observation point can be performed by converting the coordinate system, and a detailed description thereof will be omitted. An image transmitter 2718 transmits the display image data for the 2D HMD screen coordinate system to the display 2723 of the HMD via the communicator 2711.

A display 2723 of a depth sensor & HMD 2720 displays a display image from a right-eye HMD display data generator 2716 on a right-eye screen 2723*a*, and displays a display image from a left-eye HMD display data generator 2717 on a left-eye screen 2723*b*.

As described above, in this embodiment, the 3D image of the surgery target bone is used as a marker. This makes it possible to support surgery without separately creating a marker, as in the above-described embodiments.

(Data Table of Bone Surface Image Collator)

FIG. 28 is a view showing a data table 2800 used by the bone surface image collator 2713 according to this embodiment. The data table 2800 collates the depth image (distance image) that the depth sensor has acquired from the surface of the surgery target bone of the affected part of the patient with the surgery target bone stored as the preoperative preparation data 719, and determines the position and direction of the current surgery target bone.

The data table 2800 stores collated 3D bone data 2802 and a real space position and direction 2803 of the target bone determined from the collation result in association with a depth sensor image 2801 acquired by the depth sensor. The data table 2800 stores 3D bone data 2804 and 3D data 2805 of the positions and directions of a bone cutting plane and each instrument, which are obtained by 3D coordinate conversion, in correspondence with the real space position and direction 2803 of the target bone.

According to this embodiment, the 3D image of the surface of the surgery target bone is used as a marker. This makes it possible to support bone cutting without separately creating a marker, as in the above-described embodiments.

Other Embodiments

Note that in the above embodiments, bone cutting support during surgery has mainly been described. However, the same effects as described above can be obtained by applying the embodiments to support of processing that particularly needs an operation of an instrument, for example, support of another bone hole formation, support of processing of resecting a bone into a predetermined surface shape, or support of implant placement for a technique that needs to replacement with an implant.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

The present invention is applicable to a system including a plurality of devices or a single apparatus. The present invention is also applicable even when an image processing program for implementing the functions of the embodiments is supplied to the system or apparatus directly or from a remote site. Hence, the present invention also incorporates a control program installed in a computer to implement the functions of the present invention by the computer, a medium storing the control program, and a WWW (World Wide Web) server that causes a user to download the control program. Especially, the present invention incorporates at least a non-transitory computer readable medium storing a control program that causes a computer to execute processing steps included in the above-described embodiments.

This application claims the benefit of Japanese Patent Application No. 2013-123210 filed on Jun. 11, 2013, which is hereby incorporated by reference herein in its entirety.

The invention claimed is:

1. An information processing apparatus for joint replacement surgery comprising:
 a memory that stores instructions; and
 a processor that executes the instructions:
 to determine, based on 3D shape data of surgery target bones and 3D shape data of an artificial joint, 3D shape data of virtual planes along which the surgery target bones are to be cut for implanting the artificial joint, 3D shape data of virtual artificial joint and 3D shape data of virtual cut surgery target bones; and
 to overlay the determined virtual planes for cutting the surgery target bones, the virtual cut surgery target bones and the virtual artificial joint on a captured image which includes at least one marker for AR (Augmented Reality) fixed on the surgery target bones and an affected part of a patient including the surgery target bones,
 wherein after cutting the surgery target bones, the processor further executes the instruction:
 to determine, based on the 3D shape data of the virtual cut surgery target bones and the 3D shape data of the artificial joint, 3D shape data of virtual planes along which the surgery target bones are to be resected for implanting the artificial joint to the resected surgery target bones, and to overlay the determined virtual planes used for resecting the cut surgery target bones and the virtual cut surgery target bones on the captured image, wherein after resecting the cut surgery target bones, the processor further executes the instruction:

to determine, based on the 3D shape data of the virtual cut surgery target bones and the 3D shape data of the artificial joint, 3D shape data of virtual bone holes along which bone holes are to be formed in the cut surgery target bones for implanting the artificial joint using the bone holes; and to overlay the determined virtual bone holes for use in forming the bone holes in the cut surgery target bones and the virtual cut surgery target bones on the captured image, and wherein after forming the bone holes in the cut and surgery target bone, the processor further executes the instruction:

to determine, based on the 3D shape data of the virtual cut surgery target bones and the 3D shape data of the artificial joint, 3D data of the virtual artificial joint at a place at which the artificial joint is to be implanted into the cut surgery target bones; and to overlay the virtual artificial joint at the place at which the artificial joint is to be implanted with the virtual cut surgery target bones on the captured image.

2. The information processing apparatus according to claim 1, wherein the determined virtual planes include virtual bonding surfaces between the virtual artificial joint and the virtual cut surgery target bones.

3. The information processing apparatus according to claim 1, wherein the 3D shape data of the virtual artificial joint is selected among 3D models of artificial joints in a plurality of sizes.

4. The information processing apparatus according to claim 1, wherein the marker is a 3D (three dimensional) marker.

5. An information processing apparatus for joint replacement surgery comprising:

a memory that stores instructions; and a processor that executes the instructions:

to determine, based on 3D shape data of a surgery target bone and 3D shape data of an artificial joint obtained from a database, 3D shape data of virtual planes along which the surgery target bone is to be cut for implanting the artificial joint and 3D shape data of virtual separated surgery target bones obtained by cutting the surgery target bone along the virtual planes; and to overlay at least one of the virtual separated surgery target bones to be jointed with the artificial joint on a captured image which includes at least one marker for AR (Augmented Reality) fixed on the surgery target bone and an affected part of a patient including the surgery target bone, wherein after separating the surgery target bone, the processor further executes the instructions:

to determine, based on the 3D shape data of the virtual cut surgery target bones and the 3D shape data of the artificial joint, 3D shape data of virtual planes along which the surgery target bones are to be resected for implanting the artificial joint to the resected surgery target bones, and to overlay the determined virtual planes used for resecting the cut surgery target bones and the virtual cut surgery target bones on the captured image, wherein after resecting the cut surgery target bones, the processor further executes the instructions:

to determine, based on the 3D shape data of the virtual cut surgery target bones and the 3D shape data of the artificial joint, 3D shape data of virtual bone holes along which bone holes are to be formed in the cut surgery target bones for implanting the artificial joint using the bone holes; and to overlay the determined virtual bone holes for use in forming the bone holes in the cut surgery target bones and the virtual cut surgery target bones on the captured image, and wherein after forming the bone holes in the cut surgery target bones, the processor further executes the instructions:

to determine, based on the 3D shape data of the virtual cut surgery target bones and the 3D shape data of the artificial joint, 3D data of the virtual artificial joint at a place at which the artificial joint is to be implanted into the cut surgery target bones; and to overlay the virtual artificial joint at the place at which the artificial joint is to be implanted with the virtual cut surgery target bones on the captured image.

6. The information processing apparatus according to claim 5, wherein the 3D shape data of the virtual artificial joint is selected among 3D models of artificial joints in a plurality of sizes.

7. The information processing apparatus according to claim 5, wherein the marker is a 3D (three dimensional) marker.

8. An information processing method for joint replacement surgery comprising:

determining, based on 3D shape data of surgery target bones and 3D shape data of an artificial joint, 3D shape data of virtual planes along which the surgery target bones are to be cut for implanting the artificial joint, 3D shape data of virtual artificial joint and 3D shape data of virtual cut surgery target bones; and overlaying the determined virtual planes for cutting for the surgery target bones, the virtual cut surgery target bones and the virtual artificial joint on a captured image which includes at least one marker for AR (Augmented Reality) fixed on the surgery target bones and an affected part of a patient including the surgery target bones, after cutting the surgery target bones, further comprising:

determining, based on the 3D shape data of the virtual cut surgery target bones and the 3D shape data of the artificial joint, 3D shape data of virtual planes along which the surgery target bones are to be resected for implanting the artificial joint to the resected surgery target bones, and overlaying the determined virtual planes used for resecting the cut surgery target bones and the virtual cut surgery target bones on the captured image, after resecting the cut surgery target bones, further comprising:

determining, based on the 3D shape data of the virtual cut surgery target bones and the 3D shape data of the artificial joint, 3D shape data of virtual bone holes along which bone holes are to be formed in the cut surgery target bones for implanting the artificial joint using the bone holes; and overlaying the determined virtual bone holes for use in forming the bone holes in the cut surgery target bones and the virtual cut surgery target bones on the captured image, and after forming the bone holes in the cut surgery target bones, further comprising:

determining, based on the 3D shape data of the virtual cut surgery target bones and the 3D shape data of the artificial joint, 3D data of the virtual artificial joint at a place at which the artificial joint is to be implanted into the cut surgery target bones; and overlaying the virtual artificial joint at the place at which the artificial joint is to be implanted with the virtual cut surgery target bones on the captured image.

9. The information processing method according to claim 8, wherein the determined virtual planes include virtual bonding surfaces between the virtual artificial joint and the virtual cut surgery target bones.

10. The information processing method according to claim 8, wherein the 3D shape data of the virtual artificial joint is selected among 3D models of artificial joints in a plurality of sizes.

11. The information processing method according to claim 8, wherein the marker is a 3D (three dimensional) marker.

* * * * *